United States Patent
Van Hooij et al.

(10) Patent No.: US 9,453,012 B2
(45) Date of Patent: Sep. 27, 2016

(54) AMINOMETHYLENE PYRAZOLONES WITH THERAPEUTIC ACTIVITY

(71) Applicants: Compound Handling B.V., Delft (NL); Stichting Katholieke Universiteit, Nijmegen (NL)

(72) Inventors: Onno Van Hooij, Nijmegen (NL); Jacobus Antonius Schalken, Nijmegen (NL); Hendrik Engelbertus Vietor, Bussum (NL); Dennis Patrick Piet, Capelle aan den Ijssel (NL); Petrus Emmanuel Marie Maas, Delft (NL); Johann Heinrich Tijhuis, Delft (NL); Sirik Deerenberg, Delft (NL); Nanda Elisabeth Sprenkels, Delft (NL); Siu Ha Tang, The Hague (NL)

(73) Assignees: Compound Handling B.V., Delft (NL); Stichting Katholieke Universiteit, Nijmegen (NL)

( * ) Notice: Subject to any disclaimer, the term of this patent is extended or adjusted under 35 U.S.C. 154(b) by 0 days.

(21) Appl. No.: 14/383,083

(22) PCT Filed: Mar. 5, 2013

(86) PCT No.: PCT/EP2013/054449
§ 371 (c)(1),
(2) Date: Sep. 4, 2014

(87) PCT Pub. No.: WO2013/131931
PCT Pub. Date: Sep. 12, 2013

(65) Prior Publication Data
US 2015/0073019 A1    Mar. 12, 2015

(30) Foreign Application Priority Data

Mar. 6, 2012 (EP) .................... 12158253
Sep. 10, 2012 (EP) .................... 12183784

(51) Int. Cl.
*A61K 31/454* (2006.01)
*A61K 31/428* (2006.01)
(Continued)

(52) U.S. Cl.
CPC ........... *C07D 417/14* (2013.01); *A61K 31/428* (2013.01); *A61K 31/454* (2013.01); *C07D 417/04* (2013.01)

(58) Field of Classification Search
None
See application file for complete search history.

(56) References Cited

U.S. PATENT DOCUMENTS 4,909,827 A    3/1990 Gehring et al.
5,028,717 A    7/1991 Gehring et al.
(Continued)

FOREIGN PATENT DOCUMENTS

EP    0274642 A2    7/1988
WO    2004001058 A2    12/2003
(Continued)

OTHER PUBLICATIONS

Chemical Abstracts Registry No. 375835-08-8, indexed in the Registry file on STN CAS Online Dec. 17, 2001.*
(Continued)

*Primary Examiner* — Michael Barker
(74) *Attorney, Agent, or Firm* — TraskBritt, P.C.

(57) ABSTRACT

A compound having the structure according to formula III wherein: X is NH or S; $R^1$ is H or (1C-4C)alkyl; $R^2$ is (1C-4C)alkyl, phenyl or a monocyclic aromatic ring having one or more N—, O— or S— atoms in the ring, which alkyl, phenyl or aromatic ring is optionally substituted with one or more groups selected from (1C-4C)alkyl, (1C-4C)alkyloxy, halo(1C-4C)alkyl, halo(1C-4C)alkyloxy, phenyloxy, phenylthio, halogen, or nitro; $R^3$ and $R^4$ are each independently H, (1C-6C)alkyl, (2C-6C) alkenyl, (2C-6C)alkynyl, cyano, (3C-6C)cycloalkyl, phenyl, a monocyclic aromatic ring having one or more N—, O— or S— atoms in the ring, a monocyclic non-aromatic ring having one or more N—, O— or S— atoms in the ring, each optionally substituted with hydroxyl, (1C-4C)alkoxy, phenyl, cycloalkyl, piperidyl, piperazinyl, furyl, thienyl, pirazinyl, pyrrolyl, 2H-pyrrolyl, pyrazolyl, isoxazolyl, isothiazolyl, pyrrolidonyl, pyrrolinyl, imidazolinyl, imidazolyl, a monocyclic aromatic ring having one or more N—, O— or S— atoms in the ring, whereby each of these optional substituents is optionally further substituted with (1C-4C)alkyl, (1C-4C)alkyloxy, halo(1C-4C)alkyl, halo(1C-4C)alkyloxy, halogen, nitro or (1C-2C) dioxol forming a ring; or $R^3$ and $R^4$ form together pyrrolyl, imidazolyl, pyrazolyl, pyrrolidinyl, pyrrolinylimidazolidinyl, imidazolinyl, piperidyl, piperazinylmorpholinyl, each optionally substituted with (1C-6C)alkyl, phenyl(1C-4C) alkyl, phenylketo(1C-4C)alkyl; $R^5$ is H, Cl, F, Br, Me, $NO_2$, t-butyl, $OCF_3$, $OCH_3$, $CF_3$; $R^6$ is H, (1C-4C)alkyl, (1C-4C) alkyloxy, halo(1C-4C)alkyl, halo(1C-4C)alkyloxy, nitro or halogen; $R^7$ is H, F, Cl, Br, Me, $NO_2$, t-butyl, $OCF_3$, $OCH_3$, $CF_3$; or pharmaceutically acceptable addition salts thereof for use in treatments of carcinoma, in particular to delay, prevent or reverse metastasis in prostate cancer.

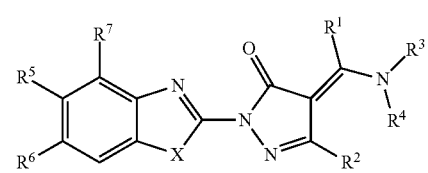

III

42 Claims, No Drawings

(51) Int. Cl.
*C07D 417/04* (2006.01)
*C07D 417/14* (2006.01)

(56) References Cited

U.S. PATENT DOCUMENTS

| | | |
|---|---|---|
| 2003/0229065 A1 | 12/2003 | Levy et al. |
| 2007/0185176 A1 | 8/2007 | Van Gelder et al. |
| 2009/0075938 A1 | 3/2009 | Wynne et al. |
| 2009/0163545 A1 | 6/2009 | Goldfarb |
| 2009/0275586 A1 | 11/2009 | Govek et al. |
| 2011/0195932 A1 | 8/2011 | Wynne et al. |
| 2012/0100609 A1 | 4/2012 | Crawford et al. |

FOREIGN PATENT DOCUMENTS

| | | |
|---|---|---|
| WO | 2005074375 A2 | 8/2005 |
| WO | 2005094805 A1 | 10/2005 |
| WO | 2007091106 A2 | 8/2007 |
| WO | 2008045664 A2 | 4/2008 |
| WO | 2009019504 A1 | 2/2009 |
| WO | 2009086303 A2 | 7/2009 |
| WO | 2010111713 A2 | 9/2010 |
| WO | 2010118347 A2 | 10/2010 |
| WO | 2013131931 A1 | 9/2013 |

OTHER PUBLICATIONS

Wu et al., Dynamic Modeling of Human 5-Lipoxygenase-Ihibitor Interactions Helps to Discover Novel Inhibitors, Journal of Medicinal Chemistry, Mar. 1, 2012, pp. 2597-2605.

Database, Chemical Abstracts Service, Columbus, Ohio, Us, Goldfarb, David Scott, Method using lifespan-altering compounds for altering the lifespan of eukaryotic organisms, and screening for such compounds, XP002676616, 2009, Database accession No. 2009:875997.

PCT International Search Report and Written Opinion, PCT/EP2013/054449, dated May 3, 2013.

PCT International Preliminary Report on Patentability, PCT/EP2013/054449 dated Sep. 9, 2014.

\* cited by examiner

AMINOMETHYLENE PYRAZOLONES WITH THERAPEUTIC ACTIVITY

FIELD OF THE INVENTION

The invention is in the field of medicinal treatment of carcinoma, in particular by using a compound with a core structure of aminomethylene pyrazolone.

BACKGROUND OF THE INVENTION

Carcinomas, which are cancers that originate from epithelial tissues, comprise the most dangerous types of cancers. Gastric, bladder and esophageal cancer are examples of carcinomas of epithelial origin. Glandular tissue often is of epithelial origin, so that breast cancer, prostate cancer and pancreas cancer also belong to the group of cancers from epithelial origin.

If a carcinoma is diagnosed early and still localized, the disease is curable by surgery, radiation therapy with or without (neo)adjuvant and chances of survival are high (>90%). However, in early stages, cancers can grow slowly and can remain locally confined for many years without causing overt symptoms. Notorious in this respect is prostate cancer. Therefore, such types of cancer often remain undiagnosed until cancerous cells have already spread beyond the prostate into the surrounding tissues (local spread) or eventually migrate (metastasize) through the blood stream or lymphatic spread into other areas of the body.

Progressive growth of epithelial cancer and invasive metastasis involves a multistep process. Tumors can generally not grow beyond a certain size, due to a lack of oxygen and other essential nutrients. However, tumors induce blood vessel growth by secreting various growth factors which induce capillary growth into the tumor to supply nutrients, allowing for tumor expansion. This physiological process is called angiogenesis. Angiogenesis is a normal and vital process in growth and development, such as in wound healing, but also a fundamental step in the transition of tumors from small harmless clusters of cells to a malignant tumor. Angiogenesis is also required for the spread, or metastasis, of a tumor. Single cancer cells can break away from an established solid tumor, enter the blood vessel, and be carried to a distant site, where they can implant and begin the growth of a secondary tumor. Such spread to other tissues (metastasis) involves invasion of other parts of the body by mesenchymal cells. Cancer cell invasion and spread is determined by epithelial-mesenchymal-transition (EMT). The spread to other tissues is preceded by transition of the epithelial cells to mesenchymal cells, indicated as epithelial-mesenchymal transition (EMT). Thereby the incipient cancer cells acquire mesenchymal, fibroblast-like properties and show reduced intercellular adhesion and increased motility, endowing the incipient cancer cells with invasive and metastatic properties. The reversed process in which mesenchymal-to-epithelial transition (MET), creates new secondary tumors at the other sites. Many patients die when diagnosed with an aggressive form of cancer in which the cancerous cells have spread, or metastasized.

It is important to improve the efficacy of medicinal treatment by providing compounds which can interfere with the metastasis of cells, more in particular compounds that can reverse EMT or interfere with the process of EMT.

Some treatment options of carcinomas are available, but are of limited success and provide no permanent cure. For prostate or breast cancer endocrine therapy, also called hormone deprivation therapy, has long been considered as the main suppression therapy to control neoplasms. The goal is to limit the body's production of the hormones. However, current endocrine therapy does not cure prostate or breast cancer. Moreover, it has become clear that expansive growth of cancer cells that become unresponsive (resistant) to the current available endocrine therapies is inevitable. In addition, it was found that in the majority of advanced cancers the hormone receptor mediated signaling pathway is still active, even at extremely low hormone levels. At this stage, the cancer can no longer be treated with available therapy and often results in progression to a lethal disease.

New chemotherapeutic drugs demonstrating improved response rates and prolonged survival are being developed. One of the examples is docetaxel (Taxotere). Unfortunately, chemotherapy reaches all parts of the body, not just only the cancer cells. It has been established that these therapies have serious side effects. Patients will undergo low blood cell counts, nausea, vomiting, abdominal pain, diarrhea, hair loss, impotence, incontinence and other unwanted symptoms. Hence, the side effects significantly hamper the quality of life of the patients. Many scientists are convinced that this treatment will offer little room for future improvements and has come close to the end of its product life cycle. Docetaxel is the current standard of care for patients that are unresponsive to the currently available endocrine therapies. In view of limited curative potential of docetaxel, and also in view of better understanding of the underlying etiology of the disease and improved early diagnosis, there is an urgent need for novel treatment strategies to prevent the progression, treat the tumor and avoid metastasis of this disease. In the present invention new compounds and a new use of such compounds for use in these novel treatment strategies are found within a chemical group with a core structure of 4-(aminomethylene)-2-(2-benzothiazolyl)-2,4-dihydro-3H-pyrazol-3-one or 4-(aminomethylene)-2-(1H-benzimidazol-2-yl)-2,4-dihydro-3H-pyrazol-3-one. In Wu et al (J. Med Chem, vol 55-2597-2605; 2012) a compound 2-(2-benzothiazolyl)-4-[1-[[(3,4-dichlorphenyl)methyl]amino]ethylidene]-2,4-dihydro-5-(trifluoromethyl)-3H-pyrazol-3-one is drawn in a table, whereby some weak activity in one of the used biochemical assays for inhibition of 5-lipoxygenase is displayed. The activity is not confirmed in a second assay, so a speculative link to any therapeutic activity cannot be justified from this information. In published texts on suggested inhibitors of O-linked and N-linked glycan glycosylation two structures of compounds within this chemical group, namely 2-(2-benzothiazolyl)-4-[1-[(2-ethoxyphenyl)amino]ethylidene]-2,4-dihydro-5-phenyl-3H-pyrazol-3-one and 2-(2-benzothiazolyl)-2,4-dihydro-4-[[[(4-methoxyphenyl])methyl]amino]methylene]-5-phenyl-3H-pyrazol-3-one are drawn without indicating a method of synthesis. In this context the possibility is discussed of therapeutic activity of such inhibitors, but such a target is not plausibly validated as model for any treatment target. Compounds with the mentioned core structures seem also to have been passed in screening tests with targets for anti-infective effects (US20030229065), for: 'Life span prolongation' (WO2009086303, US2009,163545), for herbicide and fungicide activity (EP0274642), for muscular dystrophy (WO2007/091106) and for anti-inflammatory effects by phosphodiesterase inhibition (PDE4) (WO2008/045664). In WO2005,094805 the compound 2-(2-benzothiazolyl)-4-[(dimethylamino)methylene]-2,4-dihydro-5-methyl-3H-pyrazol-3-one is used as synthesis intermediate. In compounds in Reis et al (Eur J Med Chem vol 46 pp 1448-1452, 2011) the aminomethylene pyrazolone structure may be recognized in a fixed structure of pyrazoloquinolinones. None of these disclosures reach out to the present invention.

SUMMARY OF THE INVENTION

The present invention provides for compounds having the structure according to formula I

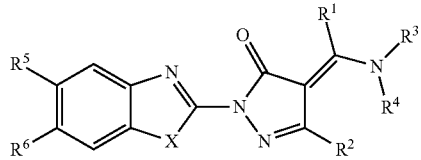

formula I wherein:
X is NH or S;
$R^1$ is H or (1C-4C)alkyl;
$R^2$ is (1C-4C)alkyl, phenyl or a monocyclic aromatic ring having one or more N—, O— or S— atoms in the ring, which alkyl, phenyl or aromatic ring is optionally substituted with one or more groups selected from (1C-4C)alkyl, (1C-4C)alkyloxy, halo(1C-4C)alkyl, halo(1C-4C)alkyloxy, phenyloxy, phenylthio, halogen, or nitro;
$R^3$ and $R^4$ are each independently H, (1C-6C)alkyl, (2C-6C) alkenyl, (2C-6C)alkynyl, cyano, (3C-6C)cycloalkyl, phenyl, a monocyclic aromatic ring having one or more N—, O— or S— atoms in the ring, a monocyclic non-aromatic ring having one or more N—, O— or S— atoms in the ring, each optionally substituted with hydroxyl, (1C-4C) alkoxy, phenyl, cycloalkyl, piperidyl, piperazinyl, furyl, thienyl, pirazinyl, pyrrolyl, 2H-pyrrolyl, pyrazolyl, isoxazolyl, isothiazolyl, pyrrolidonyl, pyrrolinyl, imidazolinyl, imidazolyl, a monocyclic aromatic ring having one or more N—, O— or S— atoms in the ring, whereby each of these optional substituents is optionally further substituted with (1C-4C)alkyl, (1C-4C)alkyloxy, halo(1C-4C)alkyl, halo (1C-4C)alkyloxy, halogen, nitro or (1C-2C)dioxol forming a ring; or
$R^3$ and $R^4$ form together pyrrolyl, imidazolyl, pyrazolyl, pyrrolidinyl, pyrrolinylimidazolidinyl, imidazolinyl, piperidyl, piperazinylmorpholinyl, each optionally substituted with (1C-6C)alkyl, phenyl(1C-4C)alkyl, phenylketo(1C-4C)alkyl;
$R^5$ is H or CF3;
$R^6$ is H, (1C-4C)alkyl, (1C-4C)alkyloxy, halo(1C-4C) alkyl, halo(1C-4C)alkyloxy, nitro or halogen;
and pharmaceutically acceptable addition salts thereof.

Such compounds may advantageously be used for therapy, i.e. the prevention or treatment of a disease. More in particular they may be used in the prevention or treatment of a carcinoma. Even more in particular the compounds according to the invention may be used in the treatment or prevention of metastasis of a carcinoma.

The term carcinoma is used herein to indicate a cancer of epithelial origin, more in particular a disease selected from the group consisting of gastric cancer, bladder cancer, esophageal cancer, breast cancer, prostate cancer or pancreas cancer. In particular the use for the treatment or prevention of metastasis of prostate cancer is preferred.

In a more specific embodiment, the invention is directed to a compound having the structure and meanings of symbols according to formula I and wherein $R^3$ and $R^4$ are independently hydrogen, methyl, ethyl, or propyl or a group as represented in the following list of structures:

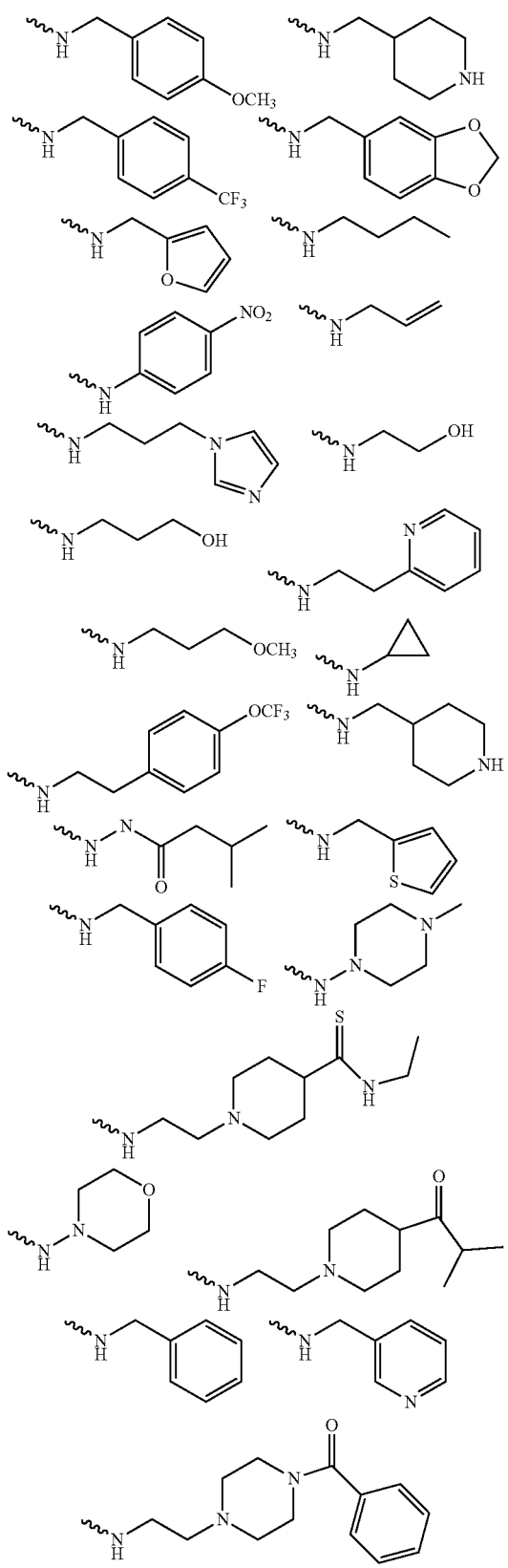

or $R^3$ ad $R^4$ form together an optionally substituted ring as represented in the following structures

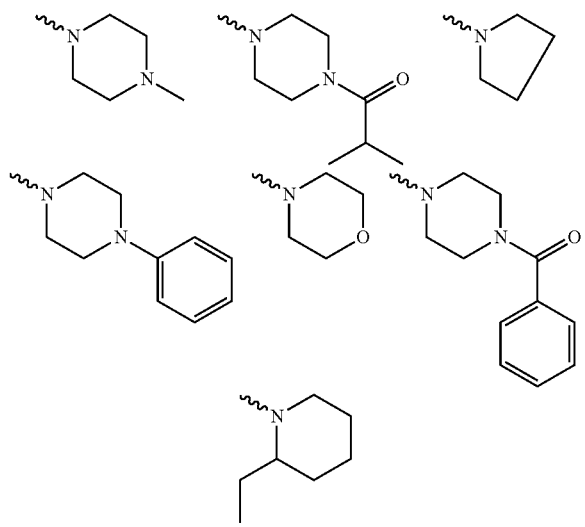

Other embodiments of the invention are compounds according to the above defined embodiments, but therein $R^1$ is H or (1C-4C)alkyl
$R^2$ is (1C-4C)alkyl, phenyl or a monocyclic aromatic ring having one or more N—, O— or S— atoms in the ring, which alkyl, phenyl or aromatic ring is optionally substituted with one or more groups selected from (1C-4C)alkyl, $OCF_3$ or halogen;
and $R^5$ and $R^6$ are hydrogen; or pharmaceutically acceptable addition salts thereof.

Preferred embodiments of the invention are as those defined above but wherein the meaning of X is S.

Other preferred embodiments are those as defined above, wherein $R^1$ is H or (1C-4C)alkyl and wherein $R^2$ is (1C-4C)alkyl or phenyl.

Other preferred embodiments are the embodiments as defined above wherein $R^3$ and $R^4$ are both methyl or wherein $R^3$ is hydrogen and $R^4$ is as defined in the respective embodiments above.

More specific embodiments are those as defined above, but wherein $R^6$ is (1C-4C)alkyl, (1C-4C)alkyloxy, halo(1C-4C)alkyl, halo(1C-4C)alkyloxy, nitro or halogen;

Another preferred embodiment of the invention is a compound according to formula II:

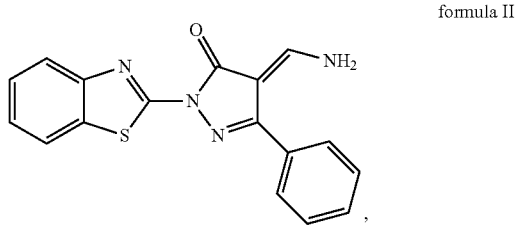 [SMILES: N/C=C1/C(=O)N(c2nc3ccccc3s2)N=C1c1ccccc1]

formula II or a pharmaceutically acceptable addition salt thereof.
In another embodiment of the invention the compound is having the structure according to formula I
wherein:
X is NH or S;
$R^1$ is H or (1C-4C)alkyl;

$R^2$ is —Z or —Y—Z, wherein Y is —CH$_2$— or —CH$_2$—CH$_2$—, and Z is phenyl or a monocyclic aromatic ring having one or more N—, O— or S— atoms in the ring, optionally substituted with one or more groups selected from (1C-4C)alkyl, (1C-4C)alkyloxy, halo(1C-4C)alkyl, halo(1C-4C)alkyloxy, phenyloxy, phenylthio, halogen, or nitro from (1C-4C)alkyl, (1C-4C)alkyloxy, halo(1C-4C)alkyl, halo(1C-4C)alkyloxy, phenyloxy, phenylthio, halogen, or nitro
or Z is thien-2-yl, optionally substituted at position 3, 4 or 5 with halogen
or Z is N-methylpyrol-3-yl or benzo[b]thien-2-yl or 2-naphthalenyl;
$R^3$ and $R^4$ are each independently H, (1C-6C)alkyl, (2C-6C)alkenyl, (2C-6C)alkynyl, cyano, (3C-6C)cycloalkyl, phenyl, a monocyclic aromatic ring having one or more N—, O— or S— atoms in the ring, a monocyclic non-aromatic ring having one or more N—, O— or S— atoms in the ring, each optionally substituted with hydroxyl, (1C-4C)alkoxy, phenyl, cycloalkyl, piperidyl, piperazinyl, furyl, thienyl, pirazinyl, pyrrolyl, 2H-pyrrolyl, pyrazolyl, isoxazolyl, isothiazolyl, pyrrolidonyl, pyrrolinyl, imidazolinyl, imidazolyl, a monocyclic aromatic ring having one or more N—, O— or S— atoms in the ring, whereby each of these optional substituents is optionally further substituted with (1C-4C)alkyl, (1C-4C)alkyloxy, halo(1C-4C)alkyl, halo(1C-4C)alkyloxy, halogen, nitro or (1C-2C)dioxol forming a ring;
or $R^3$ and $R^4$ form together pyrrolyl, imidazolyl, pyrazolyl, pyrrolidinyl, pyrrolinylimidazolidinyl, imidazolinyl, piperidyl, piperazinylmorpholinyl, each optionally substituted with (1C-6C)alkyl, phenyl(1C-4C)alkyl, phenylketo (1C-4C)alkyl;
$R^5$ is H or $CF_3$;
$R^6$ is H, (1C-4C)alkyl, (1C-4C)alkyloxy, halo(1C-4C)alkyl, halo(1C-4C)alkyloxy, nitro or halogen;
or pharmaceutically acceptable addition salts thereof.

In a preferred embodiment the compound is having the structure according the formula I, whereby X is S; $R^1$ is H; $R^2$ is Z and Z is phenyl, optionally substituted at meta or para position, or at both positions, with one or two substituents selected from the list consisting of —NO$_2$, halogen, CF$_3$, (1C-4C)alkyl and methoxy; or Z is thien-2-yl, optionally substituted at position 3, 4 or 5 with halogen; or Z is N-methylpyrol-3-yl or benzo[b]thien-2-yl or 2-naphthalenyl; $R^3$, $R^4$ are H,H or H,CH$_3$ or CH$_3$,CH$_3$; $R^5$ is H; and $R^6$ is H, halogen or methoxy;

In another embodiment the compound is defined as in the previous paragraph, but $R^2$ is phenyl, optionally substituted at meta or para position, or at both positions, with one or two substituents selected from the list consisting of halogen, CF$_3$, (1C-4C)alkyl and methoxy or $R^2$ is thien-2-yl, optionally substituted at position 3, 4 or 5 with halogen or $R^2$ is N-methylpyrol-3-yl or benzo[b]thien-2-yl or 2-naphthalenyl;

In another embodiment of the invention the compound is having the structure according to formula III

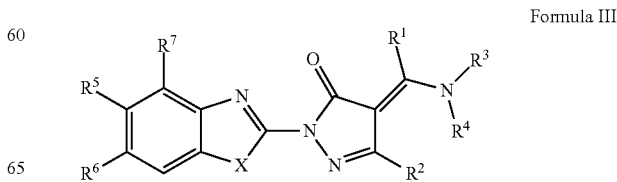

Formula III wherein:

X is NH or S;

R$^1$ is H or (1C-4C)alkyl;

R$^2$ is —Z or —Y—Z, wherein Y is —CH$_2$— or —CH$_2$—CH$_2$—, and Z is phenyl or a monocyclic aromatic ring having one or more N—, O— or S— atoms in the ring, optionally substituted with one or more groups selected from (1C-4C)alkyl, (1C-4C)alkyloxy, halo(1C-4C)alkyl, halo(1C-4C)alkyloxy, phenyloxy, phenylthio, halogen, or nitro from (1C-4C)alkyl, (1C-4C)alkyloxy, halo(1C-4C)alkyl, halo(1C-4C)alkyloxy, phenyloxy, phenylthio, halogen, or nitro or Z is thien-2-yl, optionally substituted at position 3, 4 or 5 with halogen or Z is N-methylpyrol-3-yl or benzo[b]thien-2-yl or 2-naphthalenyl;

R$^3$ and R$^4$ are each independently H, (1C-6C)alkyl, (2C-6C)alkenyl, (2C-6C)alkynyl, cyano, (3C-6C)cycloalkyl, phenyl, a monocyclic aromatic ring having one or more N—, O— or S— atoms in the ring, a monocyclic non-aromatic ring having one or more N—, O— or S— atoms in the ring, each optionally substituted with hydroxyl, (1C-4C)alkoxy, phenyl, cycloalkyl, piperidyl, piperazinyl, furyl, thienyl, pirazinyl, pyrrolyl, 2H-pyrrolyl, pyrazolyl, isoxazolyl, isothiazolyl, pyrrolidonyl, pyrrolinyl, imidazolinyl, imidazolyl, a monocyclic aromatic ring having one or more N—, O— or S— atoms in the ring, whereby each of these optional substituents is optionally further substituted with (1C-4C)alkyl, (1C-4C)alkyloxy, halo(1C-4C)alkyl, halo(1C-4C)alkyloxy, halogen, nitro or (1C-2C) dioxol forming a ring;

or R$^3$ and R$^4$ form together pyrrolyl, imidazolyl, pyrazolyl, pyrrolidinyl, pyrrolinylimidazolidinyl, imidazolinyl, piperidyl, piperazinylmorpholinyl, each optionally substituted with (1C-6C)alkyl, phenyl(1C-4C)alkyl, phenylketo(1C-4C)alkyl;

R$^5$ is H, Cl, F, Br, Me, NO$_2$, t-butyl, OCF$_3$, OCH$_3$, CF$_3$;

R$^6$ is H, (1C-4C)alkyl, (1C-4C)alkyloxy, halo(1C-4C)alkyl, halo(1C-4C)alkyloxy, nitro or halogen;

R$^7$ is H, F, Cl, Br, Me, NO$_2$, t-butyl, OCF$_3$, OCH$_3$, CF$_3$, or pharmaceutically acceptable addition salts thereof.

In a more specific embodiment the compound is having the structure according the formula III, whereby X is S; R$^1$ is H; R$^2$ is Z and Z is phenyl, optionally substituted at meta or para position, or at both positions, with one or two substituents selected from the list consisting of —NO$_2$, halogen, CF$_3$, (1C-4C)alkyl and methoxy; or Z is thien-2-yl, optionally substituted at position 3, 4 or 5 with halogen; or Z is N-methylpyrol-3-yl or benzo[b]thien-2-yl or 2-naphthalenyl; R$^3$, R$^4$ are H,H or H,CH$_3$ or CH$_3$,CH$_3$; R$^5$ is H; and R$^6$ is H, halogen or methoxy; R$^7$ is H or Cl.

In all of the above described embodiments, excepting in those whereby R$^6$ is H, the compound has preferably R$^6$ being methoxy.

Another, more specified embodiment of the invention is a compound according to Formula III
wherein X is S;
R$^1$ is H, CH$_3$;
R$^2$ is CF$_3$, CH$_3$, phenylethyl,

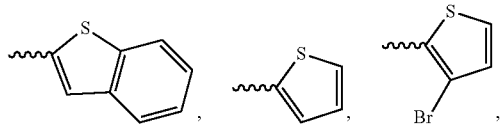

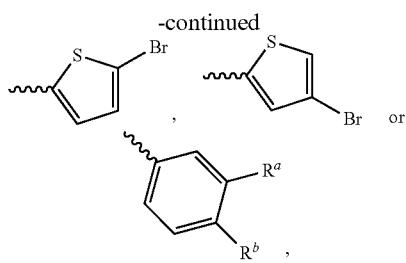

wherein R$^a$ is H, F, Cl, Br, I, NO$_2$, methyl, ethyl, isopropyl, t-butyl, methoxy or CF$_3$ and R$^b$ is H, Cl or CH$_3$;

R$^3$, R$^4$ is H, H or H, CH$_3$, or CH$_3$, CH$_3$ or one of R$^3$ or R$^4$ is —CN or p-methoxyphenylmethyl or R$^3$ and R$^4$ together represent a ring

on the nitrogen of Formula III to represent a piperidyl or R$^3$ and R$^4$ together represent a ring

on the nitrogen of Formula III to pyrrolidinyl, or R$^3$ is methyl and R$^4$ is dichlorbenzyl

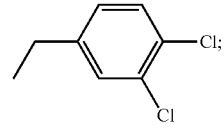

R$^5$ is H, Cl, F, Br, Me, NO$_2$, t-butyl, OCF$_3$, OCH$_3$, CF$_3$,
R$^6$ is H, F, Cl, Br, NO$_2$, CH$_3$, t-butyl, OCH$_3$, OCF$_3$, CF$_3$;
R$^7$ is H, F, Cl, Br, Me, NO$_2$, t-butyl, OCF$_3$, OCH$_3$, CF$_3$, A more preferred embodiment is a compound according to formula III, wherein
wherein X is S;
R$^1$ is H, CH$_3$;
R$^2$ is CF$_3$, CH$_3$, phenylethyl,

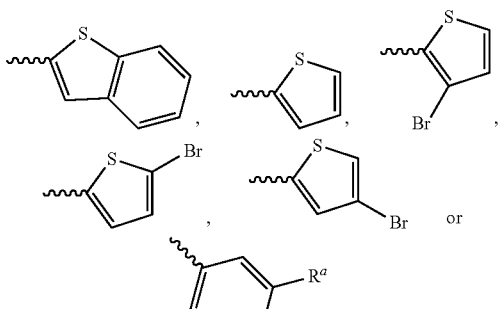

wherein $R^a$ is H, F, Cl, Br, I, $NO_2$, methyl, ethyl, isopropyl, t-butyl, methoxy or $CF_3$ and $R^b$ is H, Cl or $CH_3$;

$R^3$, $R^4$ is H, H or H, $CH_3$, or $CH_3$, $CH_3$ or one of $R^3$ or $R^4$ is —CN or p-methoxyphenylmethyl or $R^3$ and $R^4$ together represent a ring

on the nitrogen of Formula III to represent a piperidyl or $R^3$ and $R^4$ together represent a ring

on the nitrogen of Formula III to pyrrolidinyl, or $R^3$ is methyl and $R^4$ is dichlorbenzyl

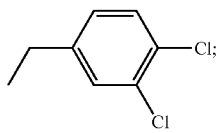

$R^5$ is H, Cl;
$R^6$ is H, F, Cl, $NO_2$, $CH_3$, t-butyl, $OCH_3$ or $OCF_3$;
$R^7$ is H, Cl.

Another more preferred embodiment is a compound according to formula III
wherein X is S;
$R^1$ is H;
$R^2$ is $CF_3$, $CH_3$, phenylethyl,

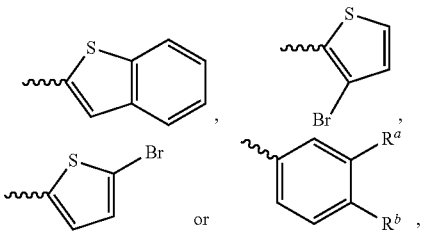

wherein $R^a$ is H, F, Cl, Br, I, $NO_2$, methyl, ethyl, isopropyl, t-butyl, methoxy or $CF_3$ and $R^b$ is H, Cl or $CH_3$;

$R^3$, $R^4$ is H, H or H, $CH_3$, or together represent a ring

on the nitrogen of Formula III to represent piperidyl, or $R^3$ is methyl and $R^4$ is dichlorbenzyl

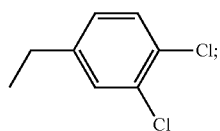

$R^5$ is H;
$R^6$ is H, Cl, $NO_2$, $CH_3$, $OCH_3$, $OCF_3$;
$R^7$ is H.

Another more specified preferred embodiment is a compound accordng to formula III,
wherein X is S;
$R^1$ is H;
$R^2$ is $CF_3$, $CH_3$,

wherein $R^a$ is H, F, Cl, Br, I, methyl, ethyl, isopropyl, t-butyl or $CF_3$ and $R^b$ is H, Cl or $CH_3$;
$R^3$, $R^4$ is H, H or H, $CH_3$, or together represent a ring

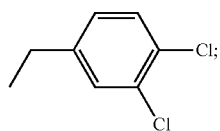

on the nitrogen of Formula III to represent piperidyl, or $R^3$ is methyl and $R^4$ is dichlorbenzyl $R^5$ is H;
$R^6$ is H, $C_1$, $NO_2$, $CH_3$, $OCH_3$, $OCF_3$;
$R^7$ is H.

In all embodiments the compounds defined comprise also their pharmaceutically acceptable addition salts.

A further embodiment of the present invention is a compound according to formula III and defined as in the embodiments with formula III above but wherein $R^3$ or $R^4$ is not p-methoxyphenylmethyl.

A compound according to the invention is also a compound for use in a treatment of carcinoma, according to formula I
wherein:
X is NH or S;
$R^1$ is H or (1C-4C)alkyl;
$R^2$ is —Z or —Y—Z, wherein Y is —$CH_2$— or —$CH_2$—$CH_2$—, and Z is phenyl or a monocyclic aromatic ring having one or more N—, O— or S— atoms in the ring, optionally substituted with one or more groups selected from (1C-4C)alkyl, (1C-4C)alkyloxy, halo(1C-4C)alkyl, halo(1C-4C)alkyloxy, phenyloxy, phenylthio, halogen, or nitro from (1C-4C)alkyl, (1C-4C)alkyloxy, halo(1C-4C)alkyl, halo(1C-4C)alkyloxy, phenyloxy, phenylthio, halogen, or nitro or Z is thien-2-yl, optionally substituted at position 3, 4 or 5 with halogen or Z is N-methylpyrol-3-yl or benzo[b]thien-2-yl or 2-naphthalenyl;

$R^3$ and $R^4$ are each independently H, (1C-6C)alkyl, (2C-6C) alkenyl, (2C-6C)alkynyl, cyano, (3C-6C)cycloalkyl, a monocyclic aromatic ring having one or more N—, O— or S— atoms in the ring, a monocyclic non-aromatic ring having one or more N—, O— or S— atoms in the ring, each optionally substituted with hydroxyl, (1C-4C) alkoxy, cycloalkyl, piperidyl, piperazinyl, furyl, thienyl, pirazinyl, pyrrolyl, 2H-pyrrolyl, pyrazolyl, isoxazolyl, isothiazolyl, pyrrolidonyl, pyrrolinyl, imidazolinyl, imidazolyl, a monocyclic aromatic ring having one or more N—, O— or S— atoms in the ring, whereby each of these optional substituents is optionally further substituted with (1C-4C)alkyl, (1C-4C)alkyloxy, halo(1C-4C)alkyl, halo (1C-4C)alkyloxy, halogen, nitro or (1C-2C)dioxol forming a ring;

or $R^3$ and $R^4$ form together pyrrolyl, imidazolyl, pyrazolyl, pyrrolidinyl, pyrrolinylimidazolidinyl, imidazolinyl, piperidyl, piperazinylmorpholinyl, each optionally substituted with (1C-6C)alkyl, phenyl(1C-4C)alkyl, phenylketo (1C-4C)alkyl;

$R^5$ is H or $CF_3$;

$R^6$ is H, (1C-4C)alkyl, (1C-4C)alkyloxy, halo(1C-4C)alkyl, halo(1C-4C)alkyloxy, nitro or halogen;

or pharmaceutically acceptable addition salts thereof.

Another embodiment of the invention is a compound according to formula I wherein:

X is NH or S;

$R^1$ is H or (1C-4C)alkyl;

$R^2$ is a monocyclic aromatic ring having one or more N—, O— or S— atoms in the ring, which aromatic ring is optionally substituted with one or more groups selected from (1C-4C)alkyl, (1C-4C)alkyloxy, halo(1C-4C)alkyl, halo (1C-4C)alkyloxy, phenyloxy, phenylthio, halogen, or nitro;

$R^3$ and $R^4$ are each independently H, (1C-4C)alkyl, (2C-6C) alkenyl, (2C-6C)alkynyl, cyano, (3C-6C)cycloalkyl, a monocyclic non-aromatic ring having one or more N—, O— or S— atoms in the ring, each optionally substituted with hydroxyl, (1C-4C)alkoxy, cycloalkyl, piperidyl, piperazinyl, furyl, thienyl, pyrrolyl, 2H-pyrrolyl, pyrazolyl, isoxazolyl, isothiazolyl, pyrrolidonyl, pyrrolinyl, imidazolinyl, imidazolyl, whereby each of these optional substituents is optionally further substituted with (1C-4C)alkyl, (1C-4C)alkyloxy, halo(1C-4C)alkyl, halo(1C-4C)alkyloxy, halogen, nitro or (1C-2C)dioxol forming a ring; or $R^3$ and $R^4$ form together pyrrolyl, imidazolyl, pyrazolyl, pyrrolidinyl, pyrrolinylimidazolidinyl, imidazolinyl, piperidyl, piperazinylmorpholinyl, each optionally substituted with (1C-6C)alkyl, phenyl(1C-4C)alkyl, phenylketo(1C-4C)alkyl;

$R^5$ is H or $CF_3$;

$R^6$ is H, (1C-4C)alkyl, (1C-4C)alkyloxy, halo(1C-4C) alkyl, halo(1C-4C)alkyloxy, nitro or halogen;

and pharmaceutically acceptable addition salts thereof.

A more specific embodiment of the invention is a compound according to formula III wherein X is S;

$R^1$ is H, $CH_3$;

$R^2$ is phenylethyl,

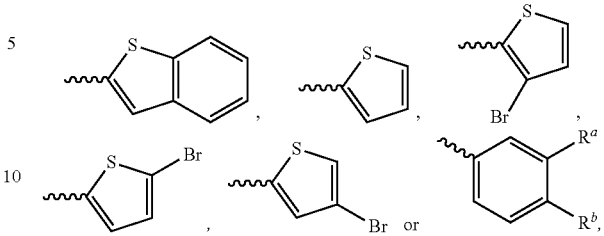

wherein $R^a$ is F, Cl, Br, I, $NO_2$, methyl, ethyl, isopropyl, t-butyl, methoxy or $CF_3$ and $R^b$ is H, $C_1$ or $CH_3$;

$R^3$, $R^4$ is H, H or H, $CH_3$, or $CH_3$, $CH_3$ or one of $R^3$ or $R^4$ is —CN or p-methoxyphenylmethyl or $R^3$ and $R^4$ together represent a ring

on the nitrogen of Formula III to represent a piperidyl or $R^3$ and $R^4$ together represent a ring

on the nitrogen of Formula III to pyrrolidinyl, or $R^3$ is methyl and $R^4$ is dichlorbenzyl

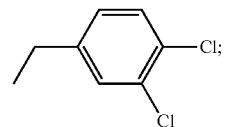

$R^5$ is H, Cl, F, Br, Me, $NO_2$, t-butyl, $OCF_3$, $OCH_3$, $CF_3$; preferred is $R^5$ is H, Cl;

$R^6$ is H, F, Cl, Br, $NO_2$, $CH_3$, t-butyl, $OCH_3$, $OCF_3$, $CF_3$;

$R^7$ is H, F, Cl, Br, Me, $NO_2$, t-butyl, $OCF_3$, $OCH_3$, $CF_3$; preferred is $R^7$ is H or Cl.

Most preferred is a compound according to formula III wherein X is S;

$R^1$ is H;

$R^2$ is

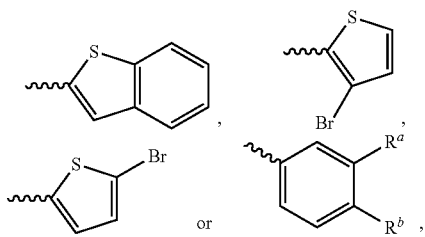

wherein $R^a$ is F, Cl, Br, I, methyl, ethyl, isopropyl, t-butyl or $CF_3$ and $R^b$ is H, Cl or $CH_3$;

$R^3$, $R^4$ is H, H or H, $CH_3$, or together represent a ring

on the nitrogen of Formula III to represent piperidyl, or $R^3$ is methyl and $R^4$ is dichlorbenzyl

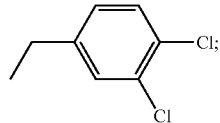

$R^5$ is H;
$R^6$ is H, $C_1$, $NO_2$, $CH_3$, $OCH_3$, $OCF_3$;
$R^7$ is H.

When embodiments are defined as characteristics of a compound this invention also provides for the use of the compounds in therapy, more specifically carcinoma, as are gastric cancer, bladder cancer, esophageal cancer, breast cancer, prostate cancer or pancreas cancer and in particular for patients wherein metastasis of the carcinoma, in particular prostate cancer, is diagnosed.

DETAILED DESCRIPTION OF THE INVENTION

The terms used in the description have the following meaning:

The prefix (1C-4C) refers to the number of 1-4 carbon atoms in the alkyl, alkenyl or alkynyl group. The definition includes amongst others a methyl, ethyl, propyl, isopropyl, butyl, tertiairy butyl, vinyl, ethynyl, cyclopropyl and propynyl.

Halo or halogen means fluorine, chlorine, bromine, iodine.

Haloalkyl, haloalkenyl or haloalkynyl means respectively an alkyl, alkenyl and alkynyl substitued with one or more halogens.

A pharmaceutically acceptable addition salt is known in the art of pharmaceutics, such as a chloride, maleate, lactate etc.

It should be realized that the compounds according to the invention exist in tautomeric isomers when $R^3$ and/or $R^4$ are hydrogen. As shown in the formulas A, B and C below the double bond system over the aminomethylenepyrazolone [A] can shift to the iminomethylpyrazolone system in [B] so that the delocalized representation as in formula [C] would be an equivalent manner to represent the compounds according to the invention. Anyway, these tautomeric isomers are comprised into the definition of the compounds according to the invention as defined with the support of the formulas.

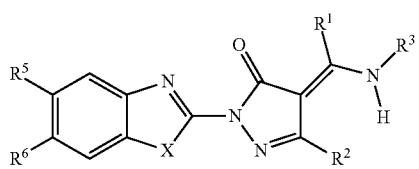
A

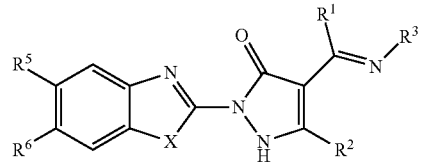
B

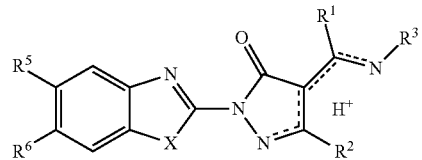
C

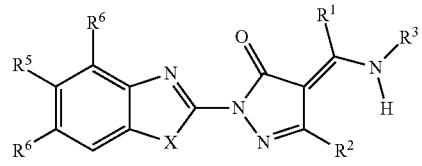
A

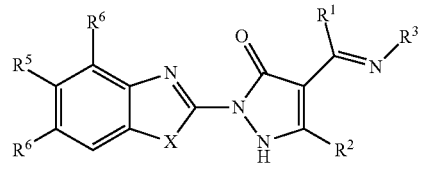
B

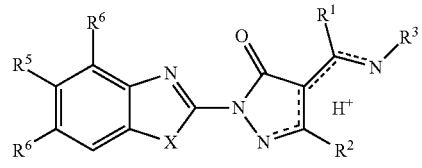
C

Furthermore, the double bond at the methylene, or methylidene if $R^1$ has an alkyl meaning, and the imino bond can be in Z or E configuration. The compound according to the invention is not specified regarding this isomerism. Only the outcome of the syntheses of specified compounds has determined and thereby implicitly defines such characteristic of particular compounds.

A compound according to the invention may be prepared, for example, by starting with preparation a 2,4-dihydropyrazol-3-one scaffold, which is synthesized through a condensation-cyclization reaction of suitable hydrazines and acetoacetate esters in either ethanol or ethanol/acetic acid mixtures at reflux temperatures where X=S and in methanol containing a catalytic amount of concentrated HCl where X=N. The cyclization product is usually collected by filtration, rinsing of the filter cake with ethanol and in vacuo drying.

In the second reaction step, the thus obtained 1,2-dihydropyrazol-3-one is subjected to an aminomethylenation reaction in THF at room temperature. The precipitated product may be purified by filtration, rinsing of the filter cake with a suitable solvent and in vacuo drying.

In the third and final step, the aminomethylidenepyrazol-3-one is treated with a suitable primary amine in methanol or ethanol at room temperature or at any temperature leading up to reflux temperature of the reaction solvent. The product may be purified by filtration and rinsing with methanol or ethanol and in vacuo drying.

A pharmaceutically acceptable addition salt of a compound may be prepared according to conventional methods.

Salts are usually obtained by combining the free base with inorganic or organic acids such as hydrochloric, fumaric, maleic, citric or succinic acid.

The therapeutic or preventive effect of a compound according to the invention can be obtained by administration of the compound to a patient (human or animal, male or female) in need of treatment by administering the compound either topically, locally or systemically. Any enteral or parenteral route, such as transdermal, transmucosal, oral, rectal, intravenous, intramuscular or subcutaneous, can be selected as most suitable under the circumstances of the condition of the patient and the location of cancer cells. The administration will be greatly aided by the manufacture of pharmaceutical compositions comprising a compound according to the invention. A pharmaceutical formulation of a compound according to the invention can be prepared according to methods known in the art, varying from conventional pills, tablets and solutions to more sophisticated formulations for depot formulations or formulations adapted for particular routes of administration. Resorption of the compound according to the invention by the patient can be facilitated or delayed by pharmaceutical additives.

In therapeutic use it is possible to select particular regimes of administration for continuous or multiple dosing per day, or for detailed treatment regimes for a certain period of time, for example a week, a month or other continuous or intermittent periods. In the field of cancer therapy it is often needed or beneficial to use more than one method to combat the disease. A compound according to the invention is suitable for combination treatment with other treatments.

Dose selection depends on routes of administration and type and condition of the treated patient. The effective dose per administration or per day will usually be in the range of 0.001-1000 mg per patient, or, expressed in amount per kg patient, in particular in consideration of small weight patients (for example children or animals) between 0.0001-100 mg/kg. The preferred range is 0.01-5 mg/kg or 1-350 mg for an average human patient Without wanting to be bound by theory in the use of the invention, it was found that an important contribution to the therapeutic mechanism of compounds of the invention can reside in interference with the process of invasion into healthy tissue, as for example the interaction between prostate cancer cells and the bone micro-environment.

For determining the effectiveness of the compounds according to the invention, we employed a model assay based on the migration of cells in a migration chamber. This model is accepted in the art as providing representative data on the ability of cells to metastasize.

We found that a preferred compound according to the invention inhibits tumor cell invasion more than 25%. Particularly preferred compound also showed dose-dependent anti-invasion activity of over 40%. The compounds according to the invention are thus capable of interfering with the acquisition of an invasive phenotype in human prostate cancer by inhibiting the EMT process. The more potent compounds for this effect are most preferred in view of the reduced dosage needed for use in therapy.

| Compound | Results % inhibition of invasion in invasion assays If more values are given these are results of repeated assays |
|---|---|
| (structure 1) | 52 49 45 |
| (structure 2) | 35 |
| (structure 3) | 93 45 |

-continued

| Compound | Results % inhibition of invasion in invasion assays If more values are given these are results of repeated assays |
|---|---|
| (benzothiazole-pyrazolone with CH=NH₂ and 3-CF₃-phenyl) | 91 |
| (benzothiazole-pyrazolone with CH=NH₂ and 3-Cl-phenyl) | 91 |
| (6-Cl-benzothiazole-pyrazolone with CH=NH₂ and phenyl) | 89% |
| (benzothiazole-pyrazolone with CH=NH₂ and 3-CF₃-phenyl) | 89<br>82<br>78 |
| (benzothiazole-pyrazolone with CH=N-piperidine and methyl) | 88 |
| (benzothiazole-pyrazolone with CH=NH₂ and 3-Br-phenyl) | 87<br>76 |

-continued

| Compound | Results % inhibition of invasion in invasion assays If more values are given these are results of repeated assays |
|---|---|
| [structure: 2-(benzothiazol-2-yl)-5-(3-iodophenyl)-4-(aminomethylene)pyrazol-3-one] | 86 |
| [structure: 2-(benzothiazol-2-yl)-5-(benzothiophen-2-yl)-4-(aminomethylene)pyrazol-3-one] | 76% |
| [structure: 2-(benzothiazol-2-yl)-5-(thiophen-2-yl)-4-(methylaminomethylene)pyrazol-3-one] | 75% |
| [structure: 2-(6-nitrobenzothiazol-2-yl)-5-(3-trifluoromethylphenyl)-4-(aminomethylene)pyrazol-3-one] | 73 |
| [structure: 2-(6-methoxybenzothiazol-2-yl)-5-phenyl-4-(aminomethylene)pyrazol-3-one] | 70 |
| [structure: 2-(6-methylbenzothiazol-2-yl)-5-(3-trifluoromethylphenyl)-4-(aminomethylene)pyrazol-3-one] | 67 |

| Compound | Results % inhibition of invasion in invasion assays If more values are given these are results of repeated assays |
|---|---|
| 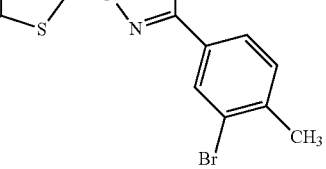 | 57% |
| 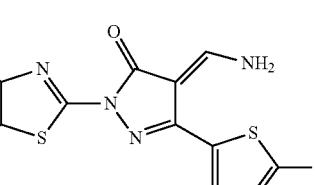 | 57 |
| 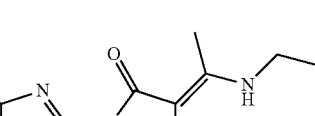 | 56 |
Further embodiments are compounds shown in the following table:
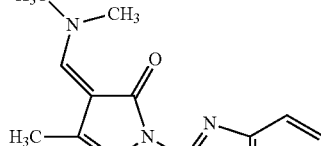
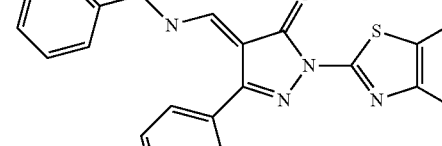
-continued
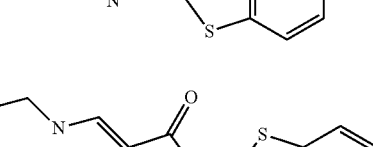
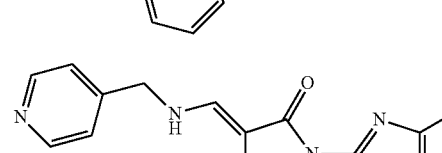

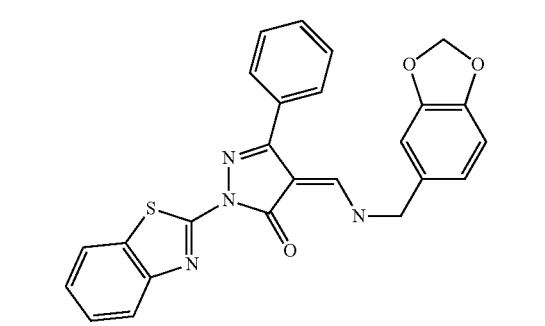 [SMILES: O=C1/C(=C\NCc2ccc3c(c2)OCO3)C(c2ccccc2)=NN1c1nc2ccccc2s1]
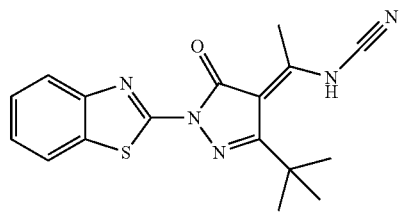 [SMILES: C/C(NC#N)=C1\C(=O)N(c2nc3ccccc3s2)N=C1C(C)(C)C]
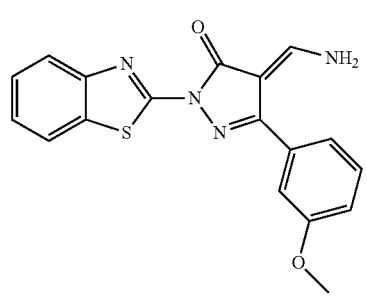 [SMILES: COc1cccc(C2=NN(c3nc4ccccc4s3)C(=O)/C2=C/N)c1]
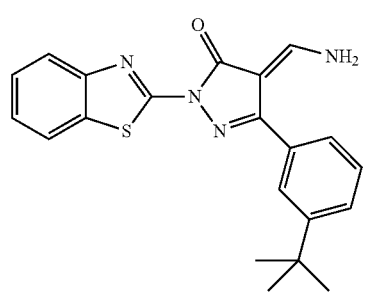 [SMILES: CC(C)(C)c1cccc(C2=NN(c3nc4ccccc4s3)C(=O)/C2=C/N)c1]
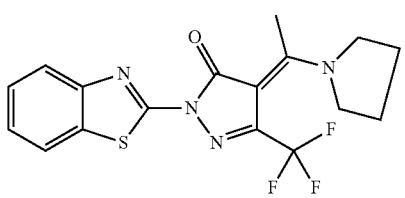 [SMILES: C/C(=C1\C(=O)N(c2nc3ccccc3s2)N=C1C(F)(F)F)N1CCCC1]
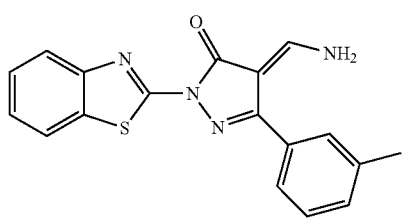 [SMILES: Cc1cccc(C2=NN(c3nc4ccccc4s3)C(=O)/C2=C/N)c1]
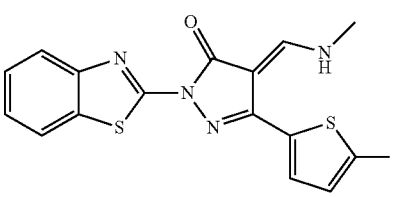
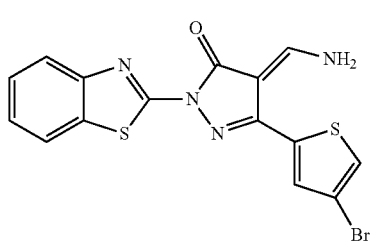 [SMILES: N/C=C1/C(=O)N(c2nc3ccccc3s2)N=C1c1cc(Br)cs1]

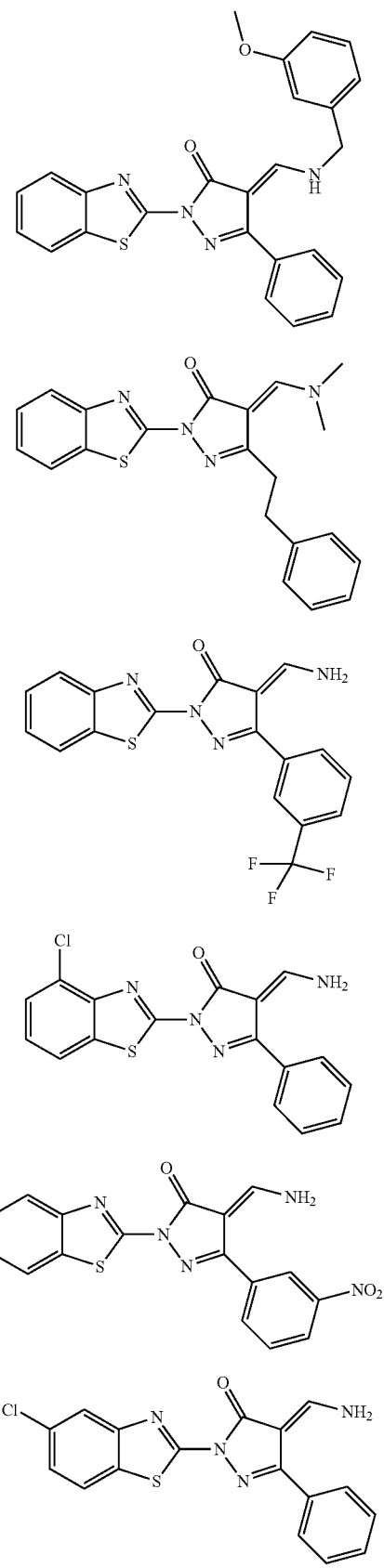
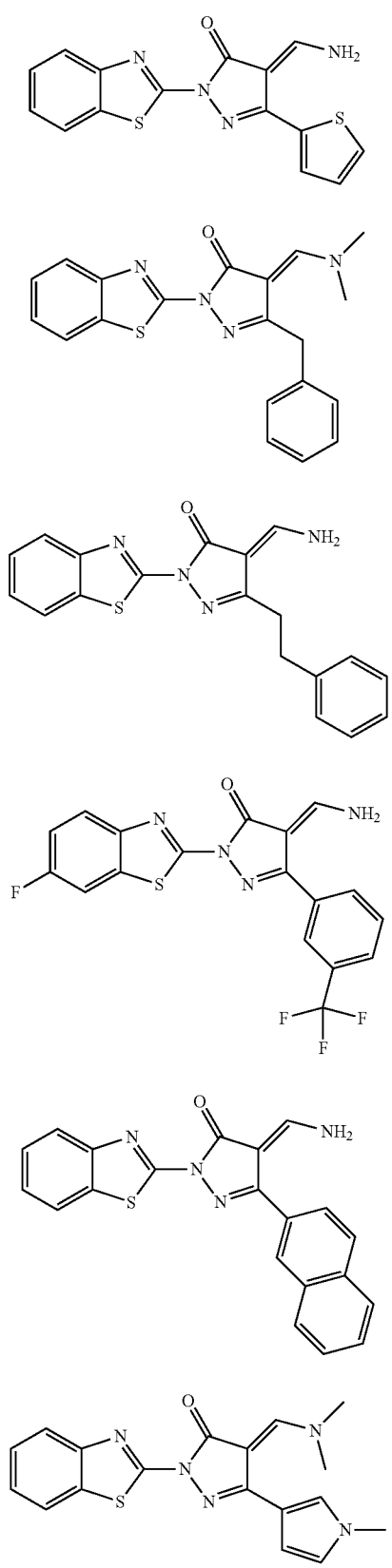

-continued

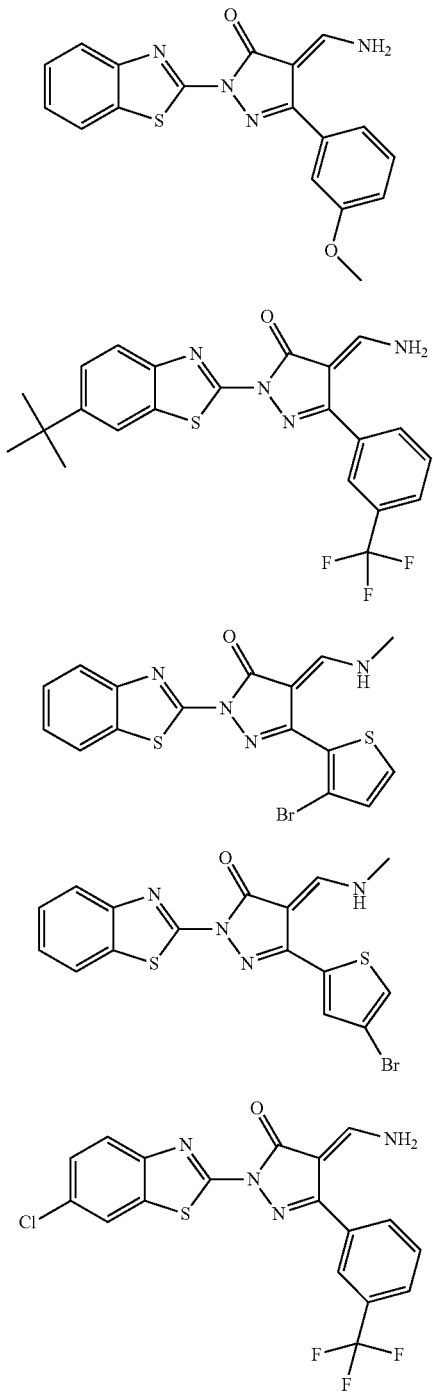

Treatment of mice with 4-[1-aminomethylidene]-2-benzothiazol-2-yl-5-phenyl-2,4-dihydro-pyrazol-3-one decreased the number of bone lesions and metastatic tumor burden. Cancer cells and tumor burden were monitored by whole body bioluminescence imaging. The data show that a compound according to the invention affects the formation of de novo skeletal metastases by PC-3M-Pro4luc+ cells in vivo. Such in vivo testing may lead to further selection, preference, deselection or disfavour of individual compounds for further programs for development of a compound for use in a prescription medicine. A particular compound of interest for such advanced testing is, 4-(aminomethylene)-2-(2-benzothiazolyl)-2,4-dihydro-5-(3-chlorophenyl)-3H-pyrazol-3-one.

EXAMPLES

Example 1

Preparation of 4-[1-Aminomethylidene]-2-benzothiazol-2-yl-5-(2-methoxyphenyl)-2,4-dihydropyrazol-3-one A solution of 1.00 g (4.45 mmol) of ethyl (2-methoxybenzoyl)acetate and 743 mg (4.45 mmol) of 2-hydrazinobenzothiazole in 15 ml of ethanol, containing a few drops of AcOH, was refluxed overnight under a nitrogen atmosphere. After evaporating the reaction solvent and replacing it with diethyl ether containing a small amount of acetone, the precipitate was filtered, washed with diethyl ether and dried to give 1.33 g (4.11 mmol, 92%) of 2-benzothiazol-2-yl-5-(2-methoxyphenyl)-1,2-dihydropyrazol-3-one. $^1$H-NMR (DMSO-d6): δ 12.40 (bs, 1H), 8.05 (d, 1H), 7.90 (d, 1H), 7.80 (s, 1H), 7.50 (m, 2H), 7.40 (t, 1H), 7.20 (d, 1H), 7.10 (m, 1H), 6.05 (s, 1H), 3.90 (s, 3H).

To a solution of 722 mg (2.23 mmol) of 2-benzothiazol-2-yl-5-(2-methoxyphenyl)-1,2-dihydropyrazol-3-one in 15 ml of THF was added N,N-dimethylformamide dimethylacetal (326 μl, 2.46 mmol). The reaction was stirred over night at room temperature under a nitrogen atmosphere after which the reaction mixture was diluted with a small amount of diethyl ether. The solids were filtered off, washed with diethyl ether and dried to give 824 mg (2.18 mmol, 98%) of 2-benzothiazol-2-yl-4-[1-dimethylaminomethylidene]-5-(2-methoxy-phenyl)-2,4-dihydropyrazol-3-one. 1H-NMR (DMSO-d6): δ 8.00 (d, 1H), 7.75 (d, 1H), 7.50 (t, 1H), 7.40 (m, 2H), 7.30 (m, 2H), 7.20 (d, 1H), 7.10 (t, 1H), 3.80 (s, 3H), 3.70 (s, 3H), 3.35 (s, 3H).

A suspension of 625 mg (1.65 mmol) of 2-benzothiazol-2-yl-4-[1-dimethylaminomethylidene]-5-(2-methoxy-phenyl)-2,4-dihydropyrazol-3-one in 10 ml ethanol and 10 ml of a 25% ammonia solution was heated to 60° C. under a nitrogen atmosphere over night. After cooling to room temperature, the reaction mixture was diluted with a little water, the solids were filtered, washed with ethanol and dried to give 481 mg (1.37 mmol, 83%) of 4-[1-aminomethylidene]-2-benzothiazol-2-yl-5-(2-methoxyphenyl)-2,4-dihydropyrazol-3-one. 1H-NMR (DMSO-d6): δ 9.40 (bs, 2H), 8.00 (d, 1H), 7.80 (d, 1H), 7.70 (s, 1H), 7.45 (m, 3H), 7.30 (t, 1H), 7.20 (d, 1H), 7.10 (t, 1H), 3.80 (s, 3H).

Example 2

Preparation of 4-[1-Aminomethylidene]-2-benzothiazol-2-yl-5-phenyl-2,4-dihydro-pyrazol-3-one A solution of 1.75 g (9.08 mmol) of ethyl benzoylacetate and 1.50 g (9.08 mmol) of 2-hydrazinobenzothiazole in 30 ml of ethanol was refluxed for 4 h under a nitrogen atmosphere. After cooling to room temperature, the precipitate was filtered, washed with cold ethanol, diethylether and dried to give 1.66 g (5.66 mmol, 62%) of 2-benzothiazol-2-yl-5-phenyl-1,2-dihydropyrazol-3-one as a white solid. $^1$H-NMR (DMSO-d6): δ 12.90 (bs, 1H), 8.05 (d, 1H), 7.90 (m, 3H), 7.50 (m, 4H), 7.30 (t, 1H), 6.10 (s, 1H).

To a solution of 190 mg (0.648 mmol) of 2-benzothiazol-2-yl-5-phenyl-1,2-dihydropyrazol-3-one in 10 ml of THF was added N,N-dimethylformamide dimethylacetal (90 μl, 0.680 mmol). The reaction was stirred for 3 h at room temperature under a nitrogen atmosphere, the solids were filtered off, washed with acetone and dried to give 125 mg (0.359 mmol, 55%) of 2-benzothiazol-2-yl-4-[1-dimethylaminomethylidene]-5-phenyl-2,4-dihydropyrazol-3-one as a yellow solid. $^1$H-NMR (DMSO-d6): δ 8.00 (d, 1H), 7.80 (d, 1H), 7.70 (s, 1H), 7.65 (m, 2H), 7.55 (m, 3H), 7.40 (t, 1H), 7.30 (t, 1H), 3.75 (s, 3H), 3.40 (s, 3H).

A suspension of 100 mg (0.287 mmol) of 2-benzothiazol-2-yl-4-[1-dimethylaminomethylidene]-5-phenyl-2,4-dihydropyrazol-3-one in 5 ml of a 25% ammonia solution was heated to 120° C. in a pressure vessel overnight. After cooling to room temperature, the solids were filtered, washed with water and dried to give 48 mg (0.150 mmol, 52%) of 4-[1-aminomethylidene]-2-benzothiazol-2-yl-5-phenyl-2,4-dihydro-pyrazol-3-one as a yellow solid. $^1$H-NMR (DMSO-d6): δ 9.05 (bs, 2H), 8.00 (m, 2H), 7.85 (d, 1H), 7.75 (m, 2H), 7.55 (m, 3H), 7.45 (t, 1H), 7.30 (t, 1H).

Example 3

Preparation of 4-[1-Aminomethylidene]-2-(1H-benzoimidazol-2-yl)-5-phenyl-2,4-dihydropyrazol-3-one A solution of 500 mg (3.37 mmol) of 2-hydrazino-1H-benzimidazole and 713 mg (3.70 mmol) of ethyl benzoylacetate of in 15 ml of methanol containing a catalytic amount of concentrated HCl. The reaction mixture was stirred at 65° C. under a nitrogen atmosphere over night. After cooling to room temperature, the precipitate was filtered and dried to give 966 mg (3.09 mmol, 92%) of 2-(1H-benzoimidazol-2-yl)-5-phenyl-1,2-dihydropyrazol-3-one as the hydrochloride salt. 1H-NMR (DMSO-d6): δ 7.95 (m, 2H), 7.65 (m, 2H), 7.45 (m, 3H), 7.20 (m 2H), 6.10 (s, 1H).

To a suspension of 100 mg (0.36 mmol) of 2-(1H-benzoimidazol-2-yl)-5-phenyl-1,2-dihydropyrazol-3-one hydrochloride salt in 5 ml of dioxane was added N,N-dimethylformamide dimethylacetal (52 µl, 0.39 mmol). The reaction was stirred for 2 h at room temperature under a nitrogen atmosphere after which the reaction mixture was cooled on an ice bath and diluted with a small amount of diethyl ether. The solids were filtered off, washed with diethyl ether and dried to give 99 mg (0.30 mmol, 83%) of 2-(1H-benzoimidazol-2-yl)-4-[1-dimethylaminomethylidene]-5-phenyl-2,4-dihydropyrazol-3-one as a yellow solid. 1H-NMR (DMSO-d6): δ 13.40 (bs, 1H), 8.55 (bs, 2H), 7.70 (s, 1H), 7.65 (m, 3H), 7.55 (m, 3H), 7.20 (m, 2H), 3.70 (s, 3H), 3.40 (s, 3H).

A suspension of 50 mg (0.15 mmol) of 2-(1H-benzoimidazol-2-yl)-4-[1-dimethylaminomethylidene]-5-phenyl-2,4-dihydropyrazol-3-one in 3 ml of a 25% ammonia solution was heated to 65° C. under a nitrogen atmosphere for 3 h. After cooling to room temperature, the solids were filtered and dried to give 32 mg (0.11 mmol, 70%) of 4-[1-aminomethylidene]-2-(1H-benzoimidazol-2-yl)-5-phenyl-2,4-dihydropyrazol-3-one as a yellow solid. $^1$H-NMR (DMSO-d6): δ 12.20 (bs, 1H), 9.40 (bs, 2H), 8.05 (m, 1H), 7.70 (m, 2H), 7.50 (m, 5H), 7.10 (m, 2H).

Example 4

Preparation of 4-[1-Aminomethylidene]-2-(4-chlorobenzothiazol-2-yl)-5-phenyl-2,4-dihydropyrazol-3-one 4-Chlorobenzothiazol-2-ylamine (5.04 g, 27.29 mmol) was suspended in 35 ml of ethylene glycol at room temperature under a nitrogen atmosphere. Hydrazine hydrate (3.98 ml, 81.87 mmol) was added followed by concentrated hydrochloric acid (2.24 ml, 27.29 mmol) and the resulting reaction mixture was heated on an oil bath to 150° C. After 1.5 h a precipitate was formed and heating was continued for an additional 1.5 h after which time the mixture was cooled, water was added and the resulting solids were filtered, washed with water and dried to give 5.33 g (26.69 mmol, 98%) of (4-chlorobenzothiazol-2-yl)-hydrazine. $^1$H-NMR (DMSO-d6): δ 9.40 (bs, 1H), 7.62 (d, 1H), 7.25 (d, 1H), 6.95 (t, 1H), 5.15 (bs, 2H).

A solution of 1.09 g (5.46 mmol) of (4-chlorobenzothiazol-2-yl)-hydrazine and 1.15 g (6.01 mmol) of ethyl benzoylacetate in 30 ml of ethanol was refluxed for 2 days under a nitrogen atmosphere. The reaction mixture was cooled and the precipitate was collected by filtration, washed with a little EtOH and dried to give 1.56 g (4.76 mmol, 87%) of 2-(4-chlorobenzothiazol-2-yl)-5-phenyl-1,2-dihydropyrazol-3-one. $^1$H-NMR (DMSO-d6): δ 12.80 (bs, 1H), 8.05 (d, 1H), 7.85 (m, 2H), 7.60-7.40 (m, 4H), 7.35 (t, 1H), 6.15 (s, 1H).

To a solution of 657 mg (2.00 mmol) of 2-(4-chlorobenzothiazol-2-yl)-5-phenyl-1,2-dihydro-pyrazol-3-one in 20 ml of THF was added N,N-dimethylformamide dimethylacetal (293 µl, 2.26 mmol). The reaction was stirred over night at room temperature under a nitrogen atmosphere after which the solids were filtered off, washed with diethyl ether and dried to give 681 mg (1.78 mmol, 89%) of 2-(4-chlorobenzothiazol-2-yl)-4-[1-dimethylaminomethylidene]-5-phenyl-2,4-dihydropyrazol-3-one. $^1$H-NMR (DMSO-d6): δ 7.95 (d, 1H), 7.60 (m, 3H), 7.55 (m, 4H), 7.25 (t, 1H), 3.75 (s, 3H), 3.40 (s, 3H).

A suspension of 545 mg (1.42 mmol) of 2-(4-chlorobenzothiazol-2-yl)-4-[1-dimethylaminomethylidene]-5-phenyl-2,4-dihydro-pyrazol-3-one in 10 ml 7N ammonia solution in MeOH was heated to 100° C. in a pressure vessel for 18 h. After cooling to room temperature, the solids were filtered, washed with a little EtOH and dried to give 460 mg (1.37 mmol, 91%) of 4-[1-aminomethylidene]-2-(4-chlorobenzothiazol-2-yl)-5-phenyl-2,4-dihydropyrazol-3-one. $^1$H-NMR (DMSO-d6): δ 9.45 (bs, 2H), 8.00 (m, 2H), 7.75 (m, 2H), 7.50 (m, 4H), 7.35 (t, 1H).

Example 5

Preparation of 4-[1-Aminomethylidene]-2-(5-chlorobenzothiazol-2-yl)-5-phenyl-2,4-dihydropyrazol-3-one 5-Chlorobenzothiazole-2-thiol (5.21 g, 25.83 mmol) was dissolved in 50 ml DMF at room temperature under a nitrogen atmosphere. To the reaction mixture were added 4.28 g (31.00 mmol) of potassium carbonate and 1.93 ml (31.00 mmol) of methyl iodide and stirring was continued over night after which time TLC (silica, 25% EtOAc in PE 40/60) indicated complete consumption of the starting material. Water was added to the reaction mixture and the resulting solids were filtered off, washed with water and dried to give 5.35 g (24.80 mmol, 96%) of 5-chloro-2-methylsulfanylbenzothiazole. $^1$H-NMR (DMSO-d6): δ 8.05 (d, 1H), 7.90 (s, 1H), 7.40 (d, 1H), 2.75 (s, 3H).

A mixture of 5-chloro-2-methylsulfanylbenzothiazole (5.03 g, 23.32 mmol) and hydrazine hydrate (11.33 ml, 233.17 mmol) in 5 ml of EtOH was heated under a nitrogen atmosphere to 100° C. After 3 h a heavy precipitation was present in the reaction mixture after which time the suspension was cooled, water was added and the resulting solids were collected, washed with water and dried to give 4.43 g (22.83 mmol, 95%) of (5-chlorobenzothiazol-2-yl)-hydrazine. $^1$H-NMR (DMSO-d6): δ 9.10 (bs, 1H), 7.65 (d, 1H), 7.30 (s, 1H), 6.95 (d, 1H), 5.10 (bs, 2H).

A solution of 935 g (4.68 mmol) of (5-chlorobenzothiazol-2-yl)-hydrazine and 990 mg (5.15 mmol) of ethyl benzoylacetate in 30 ml of ethanol was refluxed over night under a nitrogen atmosphere. The reaction mixture was cooled and the precipitate was collected by filtration, washed with a little EtOH and dried to give 970 mg (2.96 mmol, 63%) of 2-(5-chlorobenzothiazol-2-yl)-5-phenyl-1,2-dihydropyrazol-3-one. $^1$H-NMR (DMSO-d6): δ 13.00 (bs, 1H), 8.05 (d, 1H), 7.90 (m, 3H), 7.50 (m, 3H), 7.40 (t, 1H), 6.10 (s, 1H).

To a solution of 800 mg (2.44 mmol) of 2-(5-chlorobenzothiazol-2-yl)-5-phenyl-1,2-dihydro-pyrazol-3-one in 20 ml of THF was added N,N-dimethylformamide dimethylacetal (357 μl, 2.68 mmol). The reaction was stirred over night at room temperature under a nitrogen atmosphere after which ether was added and the solids were filtered off, washed with diethyl ether and dried to give 790 mg (2.06 mmol, 85%) of 2-(5-chlorobenzothiazol-2-yl)-4-[1-dimethylaminomethylidene]-5-phenyl-2,4-dihydropyrazol-3-one. $^1$H-NMR (DMSO-d6): δ 8.05 (d, 1H), 7.85 (s, 1H), 7.70 (s, 1H), 7.60-7.40 (m, 5H), 7.35 (d, 1H), 3.75 (s, 3H), 3.40 (s, 3H).

A suspension of 650 mg (1.70 mmol) of 2-(5-chlorobenzothiazol-2-yl)-4-[1-dimethylaminomethylidene]-5-phenyl-2,4-dihydropyrazol-3-one in 10 ml 7N ammonia solution in MeOH was heated to 100° C. in a pressure vessel for 24 h. After cooling to room temperature, the solids were filtered, washed with a little EtOH and dried to give 439 mg (1.38 mmol, 82%) of 4-[1-aminomethylidene]-2-(5-chlorobenzothiazol-2-yl)-5-phenyl-2,4-dihydropyrazol-3-one. $^1$H-NMR (DMSO-d6): δ 9.50 (bs, 2H), 8.05 (m, 2H), 7.90 (s, 1H), 7.75 (m, 2H), 7.50 (m, 3H), 7.40 (t, 1H).

Example 6

Preparation of 4-[1-Aminomethylidene]-2-(6-chlorobenzothiazol-2-yl)-5-phenyl-2,4-dihydropyrazol-3-one 6-Chlorobenzothiazol-2-ylamine (5.44 g, 27.84 mmol) was suspended in 35 ml of ethylene glycol at room temperature under a nitrogen atmosphere. Hydrazine hydrate (4.06 ml, 83.52 mmol) was added followed by concentrated hydrochloric acid (2.28 ml, 27.84 mmol) and the resulting reaction mixture was heated on an oil bath to 150° C. After 3 h the mixture was cooled, poured onto water and the resulting solids were filtered, washed with water and dried to give 4.98 g (24.94 mmol, 90%) of (6-chlorobenzothiazol-2-yl)-hydrazine. $^1$H-NMR (DMSO-d6): δ 9.15 (bs, 1H), 7.70 (s, 1H), 7.25 (d, 1H), 7.15 (d, 1H), 5.05 (bs, 2H).

A solution of 1.06 g (5.28 mmol) of (6-chlorobenzothiazol-2-yl)-hydrazine and 1.01 g (5.82 mmol) of ethyl benzoylacetate in 25 ml of ethanol was refluxed for 5 h under a nitrogen atmosphere. The reaction mixture was filtered while warm, washed with EtOH and dried to give 580 mg (4.76 mmol, 34%) of 2-(6-chlorobenzothiazol-2-yl)-5-phenyl-1,2-dihydropyrazol-3-one. $^1$H-NMR (DMSO-d6): δ 13.00 (bs, 1H), 8.20 (s, 1H), 7.90 (m, 3H), 7.50 (m, 4H), 6.10 (s, 1H).

To a solution of 580 mg (1.77 mmol) of 2-(6-chlorobenzothiazol-2-yl)-5-phenyl-1,2-dihydro-pyrazol-3-one in 20 ml of THF was added N,N-dimethylformamide dimethylacetal (282 μl, 2.12 mmol). The reaction was stirred for 3 h at room temperature under a nitrogen atmosphere after which the solids were filtered off, washed with diethyl ether and dried to give 628 mg (1.78 mmol, 93%) of 2-(6-chlorobenzothiazol-2-yl)-4-[1-dimethylaminomethylidene]-5-phenyl-2,4-dihydropyrazol-3-one. $^1$H-NMR (DMSO-d6): δ 8.15 (s, 1H), 7.80 (d, 1H), 7.70 (s, 1H), 7.60 (m, 2H), 7.50 (m, 3H), 7.45 (d, 1H), 3.70 (s, 3H), 3.40 (s, 3H).

A suspension of 420 mg (1.10 mmol) of 2-(6-chlorobenzothiazol-2-yl)-4-[1-dimethylaminomethylidene]-5-phenyl-2,4-dihydro-pyrazol-3-one in 10 ml 7N ammonia solution in MeOH was heated to 100° C. in a pressure vessel for 24 h. After cooling to room temperature, the solids were filtered, washed with a little EtOH and dried to give 275 mg (0.775 mmol, 70%) of 4-[1-aminomethylidene]-2-(6-chlorobenzothiazol-2-yl)-5-phenyl-2,4-dihydropyrazol-3-one. $^1$H-NMR (DMSO-d6): δ 9.50 (2bs, 2H), 8.20 (s, 1H), 8.00 (bs, 1H), 7.80 (d, 1H), 7.70 (m, 2H), 7.50 (m, 4H).

Example 7

Preparation of 4-[1-Aminomethylidene]-2-(6-methoxybenzothiazol-2-yl)-5-(3-trifluoromethylphenyl)-2,4-dihydropyrazol-3-one 6-Methoxybenzothiazol-2-ylamine (7.20 g, 40.00 mmol) was suspended in 40 ml of ethylene glycol at room temperature under a nitrogen atmosphere. Hydrazine hydrate (5.80 ml, 120.00 mmol) was added followed by concentrated hydrochloric acid (3.28 ml, 40.00 mmol) and the resulting reaction mixture was heated on an oil bath to 150° C. After 2.5 h the mixture was cooled water was added and the resulting solids were filtered, washed with water and dried to give 7.09 g (36.31 mmol, 91%) of (6-methoxybenzothiazol-2-yl)-hydrazine. $^1$H-NMR (DMSO-d6): δ 8.75 (s, 1H), 7.30 (s, 1H), 7.20 (d, 1H), 6.80 (d, 1H), 4.90 (bs, 2H), 3.70 (s, 3H).

A solution of 789 mg (4.04 mmol) of (6-methoxybenzothiazol-2-yl)-hydrazine and 9.95 mg (4.04 mmol) of methyl (3-trifluorobenzoyl)acetate in 30 ml of ethanol was refluxed for 5 h under a nitrogen atmosphere, cooled, the solids were filtered, washed with EtOH and dried to give 1.06 g (2.71 mmol, 67%) of 2-(6-methoxybenzothiazol-2-yl)-5-(3-trifluoromethylphenyl)-1,2-dihydropyrazol-3-one. $^1$H-NMR (DMSO-d6): δ 12.80 (bs, 1H), 8.20 (m, 2H), 7.80 (m, 2H), 7.70 (t, 1H), 7.60 (s, 1H), 7.10 (d, 1H), 6.20 (s, 1H), 3.80 (s, 3H).

To a solution of 458 mg (1.17 mmol) of 2-(6-methoxybenzothiazol-2-yl)-5-(3-trifluoromethylphenyl)-1,2-dihydro-pyrazol-3-one in 20 ml of THF was added N,N-dimethylformamide dimethylacetal (171 μl, 1.29 mmol). The reaction was stirred for 2 h at room temperature under a nitrogen atmosphere. Diethyl ether was added to induce precipitation. After an additional hour of stirring, the reaction volume was concentrated to ca 10% of the original volume, diethyl ether was added and the solids were filtered off, washed with diethyl ether and dried to give 450 mg (1.00 mmol, 86%) of 2-(6-methoxybenzothiazol-2-yl)-4-[1-dimethylaminomethylidene]-5-(3-trifluoromethylphenyl)-2,4-dihydropyrazol-3-one. $^1$H-NMR (DMSO-d6): δ 8.00-7.80 (m, 3H), 7.80-7.70 (m, 3H), 7.55 (s, 1H), 7.05 (d, 1H), 3.80 (s, 3H), 3.70 (s, 3H), 3.40 (s, 3H).

A suspension of 355 mg (0.725 mmol) of 2-(6-methoxybenzothiazol-2-yl)-4-[1-dimethylaminomethylidene]-5-(3-trifluoromethylphenyl)-2,4-dihydropyrazol-3-one in 10 ml 7N ammonia solution in MeOH was heated to 100° C. in a pressure vessel over night. After cooling to room temperature, the solids were filtered, washed with a little EtOH and dried to give 280 mg (0.669 mmol, 92%) of 4-[1-aminomethylidene]-2-(6-methoxybenzothiazol-2-yl)-5-(3-trifluoromethylphenyl)-2,4-dihydropyrazol-3-one. $^1$H-NMR (DMSO-d6): δ 9.50 (2bs, 2H), 8.10 (m, 3H), 7.85 (d, 1H), 7.75 (m, 2H), 7.60 (s, 1H), 7.05 (d, 1H), 3.80 (s, 3H).

Example 8

Preparation of 4-[1-Aminomethylidene]-2-benzothiazol-2-yl-5-(3-trifluoromethylphenyl)-2,4-dihydropyrazol-3-one A solution of 1.80 g (7.31 mmol) of benzothiazol-2-yl-hydrazine and 1.21 g (7.31 mmol) of 3-(3-trifluoromethylphenyl)-3-oxo-propionic acid methyl ester in 50 ml of ethanol was refluxed for 5 h under a nitrogen atmosphere, cooled, the solids were filtered, washed with EtOH and dried to give 2.12 g (5.87 mmol, 80%) of 2-benzothiazol-2-yl-5-(3-trifluoromethylphenyl)-1,2-dihydropyrazol-3-one. $^1$H-NMR (DMSO-d6): δ 13.00 (bs, 1H), 8.20 (m, 2H), 8.05 (d, 1H), 7.90 (d, 1H), 7.80 (s, 1H), 7.70 (m, 1H), 7.50 (t, 1H), 7.40 (t, 1H), 6.25 (s, 1H).

To a solution of 414 mg (1.15 mmol) of 2-benzothiazol-2-yl-5-(3-trifluoromethylphenyl)-1,2-dihydro-pyrazol-3-one in 10 ml of THF was added N,N-dimethylformamide dimethylacetal (160 μl, 1.20 mmol). The reaction was stirred for 3 h at room temperature under a nitrogen atmosphere. A small amount of diethyl ether was added and the solids were filtered off, washed with diethyl ether and dried to give 398 mg (0.956 mmol, 83%) of 2-benzothiazol-2-yl-4-[1-dimethylaminomethylidene]-5-(3-trifluoromethylphenyl)-2,4-dihydropyrazol-3-one. $^1$H-NMR (DMSO-d6): δ 8.00-7.70 (m, 7H), 7.50 (t, 1H), 7.45 (t, 1H), 3.70 (s, 3H), 3.40 (s, 3H).

A suspension of 239 mg (0.574 mmol) of 2-benzothiazol-2-yl-4-[1-dimethylaminomethylidene]-5-(3-trifluoromethylphenyl)-2,4-dihydropyrazol-3-one in 10 ml 7N ammonia solution in MeOH was heated to 100° C. in a pressure vessel over night. After cooling to room temperature, the solids were filtered, washed with a little EtOH and dried to give 163 mg (0.420 mmol, 73%) of 4-[1-aminomethylidene]-2-benzothiazol-2-yl-5-(3-trifluoromethylphenyl)-2,4-dihydropyrazol-3-one. $^1$H-NMR (DMSO-d6): δ 9.60 (bs, 2H), 8.10 (m, 4H), 7.90 (m, 2H), 7.80 (m, 1H), 7.45 (t, 1H), 7.30 (t, 1H).

Example 9

Preparation of 4-[1-Aminomethylidene]-2-benzothiazol-2-yl-5-(3-chlorophenyl)-2,4-dihydro-pyrazol-3-one A solution of 1.00 g (4.20 mmol) of benzothiazol-2-yl-hydrazine and 730 mg (4.20 mmol) of 3-(3-chlorophenyl)-3-oxopropionic acid ethyl ester in 20 ml of ethanol was refluxed over night under a nitrogen atmosphere, cooled, the solids were filtered, washed with EtOH and dried to give 1.25 g (3.81 mmol, 91%) of 2-benzothiazol-2-yl-5-(3-chlorophenyl)-1,2-dihydropyrazol-3-one. $^1$H-NMR (DMSO-d6): δ 13.00 (bs, 1H), 8.10 (d, 1H), 8.00-7.80 (m, 3H), 7.50 (m, 3H), 7.40 (t, 1H), 6.20 (s, 1H).

To a solution of 647 mg (1.97 mmol) of 2-benzothiazol-2-yl-5-(3-chlorophenyl)-1,2-dihydro-pyrazol-3-one in 15 ml of THF was added N,N-dimethylformamide dimethylacetal (288 μl, 2.17 mmol). The reaction was stirred for 2 days at room temperature under a nitrogen atmosphere. The solids were filtered off, washed with diethyl ether and dried to give 706 mg (1.84 mmol, 94%) of 2-benzothiazol-2-yl-5-(3-chlorophenyl)-4-[1-dimethylaminomethylidene]-2,4-dihydropyrazol-3-one. $^1$H-NMR (DMSO-d6): δ 8.00 (d, 1H), 7.80 (d, 1H), 7.70 (2s, 2H), 7.60 (m, 3H), 7.40 (t, 1H), 7.30 (t, 1H), 3.70 (s, 3H), 3.40 (s, 3H).

A suspension of 424 mg (1.11 mmol) of 2-benzothiazol-2-yl-5-(3-chlorophenyl)-4-[1-dimethylaminomethylidene]-2,4-dihydropyrazol-3-one in 5 ml EtOH and 20 ml of 25% aqueous ammonia solution was heated to 60° C. over night. After cooling to room temperature, the solids were filtered, washed with a little EtOH and dried to give 386 mg (1.09 mmol, 98%) of 4-[1-aminomethylidene]-2-benzothiazol-2-yl-5-(3-chlorophenyl)-2,4-dihydropyrazol-3-one. $^1$H-NMR (DMSO-d6): δ 9.60 (bs, 2H), 8.10 (s, 1H), 8.00 (d, 1H), 7.90 (s, 1H), 7.85 (d, 1H), 7.65 (m, 2H), 7.45 (m, 2H), 7.30 (t, 1H).

Example 10

Preparation of 4-[1-Aminomethylidene]-2-benzothiazol-2-yl-5-(3-methylphenyl)-2,4-dihydropyrazol-3-one A solution of 801 mg (4.85 mmol) of benzothiazol-2-yl-hydrazine and 1.00 g (4.20 mmol) of 3-(3-methylphenyl)-3-oxopropionic acid ethyl ester in 25 ml of ethanol was refluxed for 22 h under a nitrogen atmosphere, cooled, the solids were filtered, washed with a little cold EtOH and dried to give 1.41 g (4.59 mmol, 95%) of 2-benzothiazol-2-yl-5-(3-methylphenyl)-1,2-dihydropyrazol-3-one. $^1$H-NMR (DMSO-d6): δ 12.90 (bs, 1H), 8.10 (d, 1H), 7.90 (d, 1H), 7.75 (s, 1H), 7.70 (d, 1H), 7.50 (t, 1H), 7.40-7.20 (m, 4H), 6.10 (s, 1H), 2.40 (s, 3H).

To a solution of 525 mg (1.71 mmol) of 2-benzothiazol-2-yl-5-(3-methylphenyl)-1,2-dihydropyrazol-3-one in 10 ml of THF was added N,N-dimethylformamide dimethylacetal (238 μl, 1.79 mmol). The reaction was stirred for 4 h at room temperature under a nitrogen atmosphere. The solids were filtered off, washed with diethyl ether and dried to give 565 mg (1.56 mmol, 91%) of 2-benzothiazol-2-yl-5-(3-methylphenyl)-4-[1-dimethylaminomethylidene]-2,4-dihydropyrazol-3-one. $^1$H-NMR (DMSO-d6): δ 8.00 (d, 1H), 7.80 (d, 1H), 7.70 (s, 1H), 7.50-7.20 (m, 6H), 3.70 (s, 3H), 3.40 (s, 3H), 2.40 (s, 3H).

A suspension of 350 mg (0.966 mmol) of 2-benzothiazol-2-yl-5-(3-methylphenyl)-4-[1-dimethylaminomethylidene]-2,4-dihydropyrazol-3-one in 10 ml 7N ammonia solution in MeOH was heated to 100° C. in a pressure vessel over night. After cooling to room temperature, the solids were filtered, washed with a little EtOH and dried to give 300 mg (0.897 mmol, 93%) of 4-[1-aminomethylidene]-2-benzothiazol-2-yl-5-(3-methylphenyl)-2,4-dihydropyrazol-3-one. $^1$H-NMR (DMSO-d6): δ 9.45 (bs, 2H), 8.00 (m, 2H), 7.80 (d, 1H), 7.60 (s, 1H), 7.55 (d, 1H), 7.45-7.30 (m, 4H), 2.40 (s, 3H).

Example 11

Preparation of 4-[1-Aminomethylidene]-2-benzothiazol-2-yl-5-(3-methoxyphenyl)-2,4-dihydro-pyrazol-3-one A solution of 1.23 g (7.44 mmol) of benzothiazol-2-yl-hydrazine and 1.65 g (7.44 mmol) of 3-(3-methoxyphenyl)-3-oxopropionic acid ethyl ester in 40 ml of ethanol was refluxed for 5 h under a nitrogen atmosphere, cooled, the solids were filtered, washed with EtOH and dried to give 1.68 g (5.20 mmol, 70%) of 2-benzothiazol-2-yl-5-(3-methoxyphenyl)-1,2-dihydropyrazol-3-one. $^1$H-NMR (DMSO-d6): δ 13.00 (bs, 1H), 8.10 (d, 1H), 7.90 (d, 1H), 7.55-7.30 (m, 5H), 7.05 (m, 1H), 6.10 (s, 1H), 3.85 (s, 3H).

To a solution of 504 mg (1.56 mmol) of 2-benzothiazol-2-yl-5-(3-methoxyphenyl)-1,2-dihydro-pyrazol-3-one in 10 ml of THF was added N,N-dimethylformamide dimethylacetal (217 µl, 1.64 mmol). The reaction was stirred over night at room temperature under a nitrogen atmosphere. The solids were filtered off, washed with acetone and dried to give 549 mg (1.45 mmol, 93%) of 2-benzothiazol-2-yl-5-(3-methoxyphenyl)-4-[1-dimethylaminomethylidene]-2,4-dihydropyrazol-3-one. ¹H-NMR (DMSO-d6): δ 8.00 (d, 1H), 7.80 (d, 1H), 7.70 (s, 1H), 7.45 (m, 2H), 7.30 (t, 1H), 7.15 (m, 2H), 7.10 (d, 1H), 3.80 (s, 3H), 3.70 (s, 3H), 3.40 (s, 3H).

A suspension of 266 mg (0.703 mmol) of 2-benzothiazol-2-yl-5-(3-methoxyphenyl)-4-[1-dimethylaminomethylidene]-2,4-dihydropyrazol-3-one in 10 ml 7N ammonia solution in MeOH was heated to 100° C. in a pressure vessel over night. After cooling to room temperature, the solids were filtered, washed with a little EtOH and dried to give 168 mg (0.479 mmol, 68%) of 4-[1-aminomethylidene]-2-benzothiazol-2-yl-5-(3-methoxyphenyl)-2,4-dihydropyrazol-3-one. ¹H-NMR (DMSO-d6): δ 9.40 (bs, 2H), 8.00 (m, 2H), 7.85 (d, 1H), 7.45 (m, 2H), 7.40-7.20 (m, 3H), 7.10 (d, 1H), 3.80 (s, 3H).

Example 12

Preparation of 4-[1-Aminomethylidene]-2-benzothiazol-2-yl-5-(3-bromo-4-methylphenyl)-2,4-dihydropyrazol-3-one To a suspension of 376 mg NaH (9.39 mmol, 60% dispersion in mineral oil) in 30 ml of dry THF under a nitrogen atmosphere was slowly added diethyl carbonate (1.14 ml, 9.39 mmol) and 3-bromo-4-methylacetophenone (1.00 g, 4.69 mmol). The reaction mixture was heated to 70° C. for 4 h after which TLC (silica, EtOAc/PE 40-60 2:3) indicated complete consumption of the starting material. The mixture was cooled, 20 ml of water was slowly added followed by 10 drops of AcOH and extraction with 2×200 ml of EtOAc. The combined organic layers were washed with 20 ml of water, 20 ml of brine, dried over magnesium sulfate and evaporated to give 1.34 g of 3-(3-bromo-4-methylphenyl)-3-oxopropionic acid ethyl ester which was used without further purification. ¹H-NMR (CDCl3): δ 8.15 (s, 1H), 7.80 (d, 1H), 7.40 (d, 1H), 4.20 (q, 2H), 3.90 (s, 2H), 2.50 (s, 3H), 1.30 (t, 3H).

A solution of 776 mg (4.70 mmol) of benzothiazol-2-yl-hydrazine and 1.34 g (4.70 mmol) of 3-(3-bromo-4-methylphenyl)-3-oxopropionic acid ethyl ester in 15 ml of ethanol was refluxed over night under a nitrogen atmosphere, cooled, the solids were filtered, washed with a little cold EtOH and dried to give 1.80 g (4.66 mmol, 99%) of 2-benzothiazol-2-yl-5-(3-bromo-4-methylphenyl)-1,2-dihydropyrazol-3-one. ¹H-NMR (DMSO-d6): δ 12.90 (bs, 1H), 8.10 (s, 1H), 8.05 (d, 1H), 7.90 (d, 1H), 7.80 (d, 1H), 7.50 (m, 2H), 7.40 (t, 1H), 6.15 (s, 1H), 2.40 (s, 3H).

To a solution of 630 mg (1.63 mmol) of 2-benzothiazol-2-yl-5-(3-bromo-4-methylphenyl)-1,2-dihydropyrazol-3-one in 10 ml of THF was added N,N-dimethylformamide dimethylacetal (240 µl, 1.79 mmol). The reaction was stirred for 2 h at room temperature under a nitrogen atmosphere. The solids were filtered off, washed with diethyl ether and dried to give 610 mg (1.38 mmol, 85%) of 2-benzothiazol-2-yl-5-(3-bromo-4-methylphenyl)-4-[1-dimethylaminomethylidene]-2,4-dihydropyrazol-3-one. ¹H-NMR (DMSO-d6): δ 8.00 (d, 1H), 7.80 (m, 2H), 7.70 (s, 1H), 7.50 (m, 2H), 7.45 (t, 1H), 7.30 (t, 1H), 3.70 (s, 3H), 3.40 (s, 3H), 2.40 (s, 3H).

A suspension of 250 mg (0.583 mmol) of 2-benzothiazol-2-yl-5-(3-bromo-4-methylphenyl)-4-[1-dimethylaminomethylidene]-2,4-dihydropyrazol-3-one in 5 ml EtOH and 5 ml of 25% aqueous ammonia solution was heated to 60° C. over night. After cooling to room temperature, the solids were filtered, washed with a little EtOH and dried to give 185 mg (0.448 mmol, 77%) of 4-[1-aminomethylidene]-2-benzothiazol-2-yl-5-(3-bromo-4-methylphenyl)-2,4-dihydropyrazol-3-one. ¹H-NMR (DMSO-d6): δ 9.50 (bs, 2H), 8.10 (s, 1H), 8.05 (d, 1H), 7.95 (s, 1H), 7.85 (d, 1H), 7.65 (d, 1H), 7.50 (m, 2H), 7.35 (t, 1H), 2.40 (s, 3H).

Example 13

Preparation of 4-[1-Aminomethylidene]-5-benzo[b]thiophen-2-yl-2-benzothiazol-2-yl-2,4-dihydropyrazol-3-one To a suspension of 452 mg NaH (11.30 mmol, 60% dispersion in mineral oil) in 30 ml of dry THF under a nitrogen atmosphere was slowly added diethyl carbonate (1.38 ml, 11.30 mmol) and 2-acetylbenzo[b]thiophene (1.00 g, 5.67 mmol). The reaction mixture was heated to 70° C. for 3 h, cooled, 20 ml of water was slowly added followed by 10 drops of AcOH and the mixture was extracted with 3×200 ml of EtOAc. The combined organic layers were washed with 20 ml of water, 100 ml of brine, dried over magnesium sulfate and evaporated to give 1.47 g of 3-benzo[b]thiophen-2-yl-3-oxopropionic acid ethyl ester which was used without further purification. ¹H-NMR (DMSO-d6): δ 8.20 (s, 1H), 8.05 (2d, 2H), 7.55 (t, 1H), 7.50 (t, 1H), 4.25 (s, 2H), 4.10 (q, 2H), 1.20 (t, 3H).

A solution of 665 mg (4.03 mmol) of benzothiazol-2-yl-hydrazine and 1.0 g (4.70 mmol) of 3-benzo[b]thiophen-2-yl-3-oxopropionic acid ethyl ester in 10 ml of ethanol and 2 ml of HOAc was refluxed overnight under a nitrogen atmosphere, cooled, the solids were filtered, washed with a little cold EtOH and dried to give 240 mg (0.689 mmol, 17%) of 5-benzo[b]thiophen-2-yl-2-benzothiazol-2-yl-1,2-dihydropyrazol-3-one. ¹H-NMR (DMSO-d6): δ 12.90 (bs, 1H), 8.10-7.80 (m, 5H), 7.55 (t, 1H), 7.40 (m, 3H), 6.10 (s, 1H).

To a solution of 400 mg (1.15 mmol) of 5-benzo[b]thiophen-2-yl-2-benzothiazol-2-yl-1,2-dihydropyrazol-3-one in 10 ml of THF was added N,N-dimethylformamide dimethylacetal (170 µl, 1.26 mmol). The reaction was stirred over night at room temperature under a nitrogen atmosphere. The solids were filtered off, washed with THF and dried to give 286 mg (0.707 mmol, 61%) of 5-benzo[b]thiophen-2-yl-2-benzothiazol-2-yl-4-[1-dimethylaminomethylidene]-2,4-dihydropyrazol-3-one. ¹H-NMR (DMSO-d6): δ 8.10 (s, 1H), 8.05 (m, 2H), 7.90 (m, 3H), 7.50 (m, 3H), 7.35 (t, 1H), 3.75 (s, 3H), 3.55 (s, 3H).

A suspension of 100 mg (0.247 mmol) of 5-benzo[b]thiophen-2-yl-2-benzothiazol-2-yl-4-[1-dimethylaminomethylidene]-2,4-dihydropyrazol-3-one in 4 ml EtOH and 4 ml of 25% aqueous ammonia solution was heated to 60° C. for 2 h. After cooling to room temperature, the solids were filtered, washed with a little EtOH and dried to give 55 mg (0.146 mmol, 59%) of 4-[1-aminomethylidene]-5-benzo[b]thiophen-2-yl-2-benzothiazol-2-yl-2,4-dihydropyrazol-3-one. ¹H-NMR (DMSO-d6): δ 9.70 (bs, 2H), 8.50 (s, 1H), 8.10 (s, 1H), 8.05 (m, 2H), 7.90 (m, 2H), 7.50 (m, 3H), 7.35 (t, 1H).

Example 14

Preparation of 4-[1-Aminomethylidene]-2-benzothiazol-2-yl-5-thiophen-2-yl-2,4-dihydropyrazol-3-one To a suspension of 630 mg NaH (15.85 mmol, 60% dispersion in mineral oil) in 40 ml of dry toluene under a nitrogen atmosphere was slowly added diethyl carbonate (1.92 ml, 15.85 mmol) and 2-acetylthiophene (1.00 g, 7.93 mmol). The reaction mixture was heated to 70° C. for 1 h, cooled, 200 ml of water was slowly added followed by 2 ml of AcOH and the mixture was extracted with 3×200 ml of EtOAc. The combined organic layers were washed with 100 ml of water, 300 ml of brine, dried over magnesium sulfate and evaporated to give a crude oil that was purified by column chromatography (silica, 10% EtOAc in PE 40-60) to give 1.00 g (5.04 mmol, 64%) of 3-thiophen-2-yl-3-oxopropionic acid ethyl ester. $^1$H-NMR (CDCl3): δ 8.15 (s, 1H), 7.55 (m, 1H), 7.35 (m, 1H), 4.20 (q, 2H), 3.90 (s, 2H), 1.25 (t, 3H).

A solution of 870 mg (5.25 mmol) of benzothiazol-2-yl-hydrazine and 1.04 g (5.25 mmol) of 3-thiophen-2-yl-3-oxopropionic acid ethyl ester in 15 ml of ethanol was refluxed for 18 h under a nitrogen atmosphere, cooled, the solids were filtered, washed with a little cold EtOH and dried to give 1.38 g (4.61 mmol, 88%) of 2-benzothiazol-2-yl-5-thiophen-2-yl-1,2-dihydropyrazol-3-one. $^1$H-NMR (DMSO-d6): δ 12.90 (bs, 1H), 8.05 (d, 1H), 7.90 (d, 1H), 7.65 (m, 2H), 7.50 (t, 1H), 7.40 (t, 1H), 7.10 (s, 1H), 5.95 (s, 1H).

To a solution of 720 mg (2.41 mmol) of 2-benzothiazol-2-yl-5-thiophen-2-yl-1,2-dihydropyrazol-3-one in 10 ml of THF was added N,N-dimethylformamide dimethylacetal (350 µl, 2.56 mmol). The reaction was stirred for 2 h at room temperature under a nitrogen atmosphere. Diethyl ether was added to induce precipitation after which the solids were filtered off, washed with diethyl ether and dried to give 753 mg (2.12 mmol, 88%) of 2-benzothiazol-2-yl-4-[1-dimethylaminomethylidene]-5-thiophen-2-yl-2,4-dihydropyrazol-3-one as a mixture of isomers. In order to obtain one of the isomers pure, 5 ml of DCM was added to the solid isomeric mixture, stirred thoroughly and the liquid decanted from the remaining solids. The liquid was concentrated, the solids filtered and washed with 2 ml of DCM. The combined solids after two DCM washing cycles weighed 82 mg and consisted of one single isomer. $^1$H-NMR (DMSO-d6): δ 8.00 (m, 2H), 7.85 (m, 1H), 7.75 (s, 1H), 7.50 (s, 1H), 7.45 (m, 1H), 7.30 (m, 1H), 7.25 (s, 1H), 3.75 (s, 3H), 3.50 (s, 3H).

A suspension of 500 mg (1.41 mmol) of 2-benzothiazol-2-yl-4-[1-dimethylaminomethylidene]-5-thiophen-2-yl-2,4-dihydropyrazol-3-one in 5 ml EtOH and 5 ml of 25% aqueous ammonia solution was heated to 60° C. for 1 h. After cooling to room temperature, the solids were filtered, washed with a little EtOH and dried to give 357 mg (1.09 mmol, 78%) of 4-[1-aminomethylidene]-2-benzothiazol-2-yl-5-thiophen-2-yl-2,4-dihydropyrazol-3-one. $^1$H-NMR (DMSO-d6): δ 9.40 (bs, 2H), 8.30 (s, 1H), 8.05 (d, 1H), 7.90 (d, 1H), 7.75 (d, 1H), 7.65 (m, 1H), 7.50 (t, 1H), 7.35 (t, 1H), 7.25 (m, 1H).

Example 15

Preparation of 4-[1-Aminomethylidene]-2-benzothiazol-2-yl-5-(5-bromothiophen-2-yl)-2,4-dihydropyrazol-3-one To a suspension of 597 mg NaH (14.92 mmol, 60% dispersion in mineral oil) in 75 ml of dry THF under a nitrogen atmosphere was slowly added diethyl carbonate (1.81 ml, 14.92 mmol) and 2-acetyl-5-bromothiophene (1.53 g, 7.46 mmol). The reaction mixture was heated to 70° C. for 2 h, cooled, poured into iced water and acidified with AcOH. The mixture was extracted with EtOAc twice and the combined organic layers were washed with water, brine, dried over magnesium sulfate and evaporated to give 1.82 g (6.57 mmol, 88%) of 3-(5-bromothiophen-2-yl)-3-oxopropionic acid ethyl ester. $^1$H-NMR (CDCl3): δ 7.5 (d, 1H), 7.30 (s, 1H), 7.15 (d, 1H), 4.20 (q, 2H), 3.85 (s, 2H), 1.25 (t, 3H).

A solution of 1.08 g (6.57 mmol) of benzothiazol-2-yl-hydrazine and 1.82 g (6.57 mmol) of 3-(5-bromothiophen-2-yl)-3-oxopropionic acid ethyl ester in 25 ml of ethanol containing 5 ml of AcOH was refluxed overnight under a nitrogen atmosphere, cooled, the solids were filtered, washed with a little cold EtOH and dried to give 1.58 g (4.18 mmol, 64%) of 2-benzothiazol-2-yl-5-(5-bromothiophen-2-yl)-1,2-dihydropyrazol-3-one. $^1$H-NMR (DMSO-d6): δ 13.00 (bs, 1H), 8.05 (d, 1H), 7.90 (d, 1H), 7.50 (m, 2H), 7.40 (t, 1H), 7.30 (s, 1H), 6.05 (s, 1H).

To a solution of 793 mg (2.10 mmol) of 2-benzothiazol-2-yl-5-(5-bromothiophen-2-yl)-1,2-dihydropyrazol-3-one in 15 ml of THF was added N,N-dimethylformamide dimethylacetal (292 µl, 2.20 mmol). The reaction was stirred for 15 minutes at room temperature under a nitrogen atmosphere. The solids were filtered off, washed with THF and dried to give 621 mg (1.43 mmol, 68%) of 2-benzothiazol-2-yl-5-(5-bromothiophen-2-yl)-4-[1-dimethylaminomethylidene]-2,4-dihydropyrazol-3-one. $^1$H-NMR (DMSO-d6): δ 8.00 (d, 1H), 7.95 (s, 1H), 7.85 (d, 1H), 7.45 (t, 1H), 7.40-7.30 (m, 3H), 3.70 (s, 3H), 3.45 (s, 3H).

A suspension of 260 mg (0.60 mmol) of 2-benzothiazol-2-yl-5-(5-bromothiophen-2-yl)-4-[1-dimethylaminomethylidene]-2,4-dihydropyrazol-3-one in 10 ml 7N ammonia solution in MeOH was stirred at room temperature in a closed flask for 2 days followed by evaporation of the solvent to give 241 mg (0.59 mmol, 99%) of 4-[1-aminomethylidene]-2-benzothiazol-2-yl-5-(5-bromothiophen-2-yl)-2,4-dihydropyrazol-3-one. $^1$H-NMR (DMSO-d6): δ 9.60 (bs, 2H), 8.30 (s, 1H), 8.05 (d, 1H), 7.90 (d, 1H), 7.55 (m, 1H), 7.50 (t, 1H), 7.35 (m, 2H).

Example 16

4-[1-Aminomethylidene]-2-benzothiazol-2-yl-5-(3-bromophenyl)-2,4-dihydropyrazol-3-one A solution of 609 mg (3.69 mmol) of benzothiazol-2-yl-hydrazine and 1.00 g (3.69 mmol) of 3-(3-bromophenyl)-3-oxopropionic acid ethyl ester in 20 ml of EtOH was refluxed overnight under a nitrogen atmosphere, cooled, 2 ml of water was added and the solids were filtered, washed with EtOH and dried to give 1.23 g (3.30 mmol, 90%) of 2-benzothiazol-2-yl-5-(3-bromophenyl)-1,2-dihydropyrazol-3-one. $^1$H-NMR (DMSO-d6): δ 12.90 (bs, 1H), 8.10 (m, 2H), 7.90 (m, 2H), 7.65 (m, 1H), 7.50-7.30 (m, 3H), 6.20 (s, 1H).

To a solution of 470 mg (1.26 mmol) of 2-benzothiazol-2-yl-5-(3-bromophenyl)-1,2-dihydropyrazol-3-one in 10 ml of THF was added N,N-dimethylformamide dimethylacetal (185 µl, 1.39 mmol). The reaction was stirred overnight at room temperature under a nitrogen atmosphere. Diethyl ether was added and the solids were filtered off, washed with diethyl ether and dried to give 487 mg (1.13 mmol, 90%) of 2-benzothiazol-2-yl-5-(3-bromophenyl)-4-[1-dimethylaminomethylidene]-2,4-dihydropyrazol-3-one. $^1$H-NMR (DMSO-d6): δ 8.00 (d, 1H), 7.80 (m, 2H), 7.70 (m, 2H), 7.65 (d, 1H), 7.45 (2t, 2H), 7.35 (t, 1H), 3.70 (s, 3H), 3.40 (s, 3H).

A suspension of 467 mg (1.09 mmol) of 2-benzothiazol-2-yl-5-(3-bromophenyl)-4-[1-dimethylaminomethylidene]-2,4-dihydropyrazol-3-one in 10 ml 7N NH3 in MeOH was heated in a pressure vessel to 100° C. overnight. After cooling to room temperature, the solids were filtered, washed with a little EtOH and dried to give 382 mg (0.957 mmol, 88%) of 4-[1-aminomethylidene]-2-benzothiazol-2-yl-5-(3-bromophenyl)-2,4-dihydropyrazol-3-one. ¹H-NMR (DMSO-d6): δ 9.60 (bs, 2H), 8.10 (s, 1H), 8.00 (d, 1H), 7.90 (d, 1H), 7.80 (s, 1H), 7.70 (m, 1H), 7.55 (m, 2H), 7.45 (t, 1H), 7.30 (t, 1H).

Example 17

4-[1-Aminomethylidene]-2-benzothiazol-2-yl-5-(3-iodophenyl)-2,4-dihydropyrazol-3-one A solution of 519 mg (3.14 mmol) of benzothiazol-2-yl-hydrazine and 1.00 g (3.14 mmol) of 3-(3-iodophenyl)-3-oxopropionic acid ethyl ester in 20 ml of EtOH was refluxed overnight under a nitrogen atmosphere, cooled, 2 ml of water was added and the solids were filtered, washed with EtOH and dried to give 1.14 g (2.71 mmol, 86%) of 2-benzothiazol-2-yl-5-(3-iodophenyl)-1,2-dihydropyrazol-3-one. ¹H-NMR (DMSO-d6): δ 13.00 (bs, 1H), 8.25 (s, 1H), 8.05 (d, 1H), 7.90 (m, 2H), 7.80 (m, 1H), 7.50 (t, 1H), 7.40 (t, 1H), 7.30 (t, 1H), 6.20 (s, 1H).

To a solution of 393 mg (0.94 mmol) of 2-benzothiazol-2-yl-5-(3-iodophenyl)-1,2-dihydropyrazol-3-one in 20 ml of THF was added N,N-dimethylformamide dimethylacetal (137 μl, 1.03 mmol). The reaction was stirred for 1 hour at room temperature under a nitrogen atmosphere. Diethyl ether was added and the solids were filtered off, washed with diethyl ether and dried to give 424 mg (0.89 mmol, 95%) of 2-benzothiazol-2-yl-5-(3-iodophenyl)-4-[1-dimethylaminomethylidene]-2,4-dihydropyrazol-3-one. ¹H-NMR (DMSO-d6): δ 8.00 (m, 2H), 7.90 (d, 1H), 7.80 (d, 1H), 7.70 (s, 1H), 7.60 (d, 1H), 7.40 (t, 1H), 7.30 (m, 2H), 3.70 (s, 3H), 3.40 (s, 3H).

A suspension of 196 mg (0.413 mmol) of 2-benzothiazol-2-yl-5-(3-iodophenyl)-4-[1-dimethylaminomethylidene]-2,4-dihydropyrazol-3-one in 3 ml 7N NH3 in MeOH was heated to 50° C. for 1.5 hours and left to cool overnight. The solids were filtered, washed with a little EtOH and dried to give 137 mg (0.307 mmol, 74%) of 4-[1-aminomethylidene]-2-benzothiazol-2-yl-5-(3-iodophenyl)-2,4-dihydropyrazol-3-one. ¹H-NMR (DMSO-d6): δ 9.50 (bs, 2H), 8.10 (s, 1H), 8.00 (m, 2H), 7.85 (m, 2H), 7.80 (d, 1H), 7.45 (t, 1H), 7.30 (m, 2H).

Example 18

4-[1-Aminomethylidene]-2-benzothiazol-2-yl-5-(3-fluorophenyl)-2,4-dihydropyrazol-3-one A solution of 786 mg (4.76 mmol) of benzothiazol-2-yl-hydrazine and 1.00 g (4.76 mmol) of 3-(3-fluorophenyl)-3-oxopropionic acid ethyl ester in 25 ml of EtOH was refluxed for 5 hours under a nitrogen atmosphere, cooled and the solids were filtered, washed with EtOH and dried to give 870 mg (2.79 mmol, 59%) of 2-benzothiazol-2-yl-5-(3-fluorophenyl)-1,2-dihydropyrazol-3-one. ¹H-NMR (DMSO-d6): δ 13.00 (bs, 1H), 8.10 (d, 1H), 7.90 (d, 1H), 7.75 (m, 2H), 7.50 (m, 2H), 7.40 (t, 1H), 7.30 (m, 1H), 6.20 (s, 1H).

To a solution of 480 mg (1.54 mmol) of 2-benzothiazol-2-yl-5-(3-fluorophenyl)-1,2-dihydropyrazol-3-one in 10 ml of THF was added N,N-dimethylformamide dimethylacetal (225 μl, 1.70 mmol). The reaction was stirred for 3 hours at room temperature under a nitrogen atmosphere. Diethyl ether was added and the solids were filtered off, washed with diethyl ether and dried to give 520 mg (1.42 mmol, 92%) of 2-benzothiazol-2-yl-5-(3-fluorophenyl)-4-[1-dimethylaminomethylidene]-2,4-dihydropyrazol-3-one. ¹H-NMR (DMSO-d6): δ 8.00 (d, 1H), 7.80 (d, 1H), 7.70 (s, 1H), 7.60 (m, 1H), 7.50-7.40 (m, 3H), 7.40-7.30 (m, 2H), 3.70 (s, 3H), 3.40 (s, 3H).

A suspension of 360 mg (0.819 mmol) of 2-benzothiazol-2-yl-5-(3-fluorophenyl)-4-[1-dimethylaminomethylidene]-2,4-dihydropyrazol-3-one in 3 ml 7N NH3 in MeOH was heated in a pressure vessel to 100° C. overnight. After cooling to room temperature the solids were filtered, washed with a little EtOH and dried to give 249 mg (0.736 mmol, 90%) of 4-[1-aminomethylidene]-2-benzothiazol-2-yl-5-(3-fluorophenyl)-2,4-dihydropyrazol-3-one. ¹H-NMR (DMSO-d6): δ 9.40 (bs, 2H), 8.10 (s, 1H), 8.00 (d, 1H), 7.85 (d, 1H), 7.60 (m, 3H), 7.45 (t, 1H), 7.35 (m, 2H).

Example 19

4-[1-Aminomethylidene]-2-benzothiazol-2-yl-5-(3-t-butylphenyl)-2,4-dihydropyrazol-3-one To a suspension of 984 mg NaH (24.60 mmol, 60% dispersion in mineral oil) in 15 ml of dry benzene under a nitrogen atmosphere was slowly added diethyl carbonate (2.10 ml, 16.40 mmol) and 3-t-butylacetophenone (1.45 g, 8.20 mmol). The reaction mixture was heated to reflux for 30 minutes. The mixture was cooled to room temperature, 3 ml of AcOH was slowly added followed by water and extraction with EtOAc. The organic layer was dried over magnesium sulfate, evaporated and the residue was purified by column chromatography (silica, PE (40-60)/EtOAc 20:1) to give 1.45 g (5.84 mmol, 71%) of 3-(3-t-butylphenyl)-3-oxopropionic acid ethyl ester.

A solution of 964 mg (5.84 mmol) of benzothiazol-2-yl-hydrazine and 1.45 g (5.84 mmol) of 3-(3-t-butylphenyl)-3-oxopropionic acid ethyl ester in 5 ml of EtOH and 5 ml of HOAc was refluxed overnight under a nitrogen atmosphere, cooled and the solids were filtered, washed with EtOH and dried to give 1.70 g (4.86 mmol, 83%) of 2-benzothiazol-2-yl-5-(3-t-butylphenyl)-1,2-dihydropyrazol-3-one. ¹H-NMR (DMSO-d6): δ 13.05 (bs, 1H), 8.10 (d, 1H), 7.90 (m, 2H), 7.70 (d, 1H), 7.55-7.30 (m, 4H), 6.10 (s, 1H), 1.35 (s, 9H).

To a solution of 1.00 g (2.86 mmol) of 2-benzothiazol-2-yl-5-(3-t-butylphenyl)-1,2-dihydropyrazol-3-one in 20 ml of THF was added N,N-dimethylformamide dimethylacetal (4.20 μl, 3.15 mmol). The reaction was stirred for 3 hours at room temperature under a nitrogen atmosphere, the solids were filtered off, washed with diethyl ether and dried to give 690 mg (1.70 mmol, 60%) of 2-benzothiazol-2-yl-5-(3-t-butylphenyl)-4-[1-dimethylaminomethylidene]-2,4-dihydropyrazol-3-one. ¹H-NMR (DMSO-d6): δ 8.00 (d, 1H), 7.80 (d, 1H), 7.65 (s, 1H), 7.60 (s, 1H), 7.55 (m, 1H), 7.45 (m, 3H), 7.30 (t, 1H), 3.70 (s, 3H), 3.40 (s, 3H), 1.35 (s, 9H).

A suspension of 150 mg (0.371 mmol) of 2-benzothiazol-2-yl-5-(3-t-butylphenyl)-4-[1-dimethylaminomethylidene]-2,4-dihydropyrazol-3-one in 5 ml 7N NH3 in MeOH was heated to 60° C. for 2 hours. After cooling to room temperature the solids were filtered, washed with a little EtOH and dried to give 114 mg (0.302 mmol, 82%) of 4-[1- aminomethylidene]-2-benzothiazol-2-yl-5-(3-t-butylphenyl)-2,4-dihydropyrazol-3-one. $^1$H-NMR (DMSO-d6): δ 9.45 (bs, 2H), 8.05 (d, 1H), 7.95 (s, 1H), 7.85 (d, 1H), 7.70 (s, 1H), 7.60-7.40 (m, 3H), 7.30 (m, 2H), 1.35 (s, 9H).

Example 20

4-[1-Aminomethylidene]-2-(6-methoxybenzothiazol-2-yl)-5-phenyl-2,4-dihydropyrazol-3-one A solution of 1.33 g (6.81 mmol) of (6-methoxybenzothiazol-2-yl)-hydrazine and 1.44 g (7.49 mmol) of ethyl benzoylacetate in 40 ml of EtOH was refluxed overnight under a nitrogen atmosphere. The solids were filtered off, washed with EtOH and dried to give 1.96 g (6.06 mmol, 89%) of 2-(6-methoxybenzothiazol-2-yl)-5-phenyl-1,2-dihydropyrazol-3-one. $^1$H-NMR (DMSO-d6): δ 12.85 (bs, 1H), 7.85 (m, 2H), 8.00 (d, 1H), 7.65 (d, 1H), 7.45 (m, 2H), 7.10 (d, 1h), 6.10 (s, 1H), 3.80 (s, 3H).

To a solution of 364 mg (1.13 mmol) of 2-(6-methoxy-benzothiazol-2-yl)-5-phenyl-1,2-dihydropyrazol-3-one in 15 ml of THF was added N,N-dimethylformamide dimethylacetal (164 µl, 1.24 mmol). The reaction was stirred overnight at room temperature under a nitrogen atmosphere after which the solids were filtered off, washed with diethyl ether and dried to give 372 mg (0.983 mmol, 87%) of 2-(6-methoxybenzothiazol-2-yl)-4-[1-dimethylaminomethylidene]-5-phenyl-2,4-dihydropyrazol-3-one. $^1$H-NMR (DMSO-d6): δ 7.70-7.45 (m, 8H), 7.00 (d, 1H), 3.80 (s, 3H), 3.70 (s, 3H), 3.40 (s, 3H).

A suspension of 240 mg (0.634 mmol) of 2-(6-methoxy-benzothiazol-2-yl)-4-[1-dimethylaminomethylidene]-5-phenyl-2,4-dihydropyrazol-3-one in 10 ml 7N NH3 in MeOH was heated to 100° C. in a pressure vessel overnight. After cooling to room temperature, the solids were filtered, washed with a little EtOH and dried to give 192 mg (0.548 mmol, 86%) of 4-[1-aminomethylidene]-2-(6-methoxybenzothiazol-2-yl)-5-phenyl-2,4-dihydropyrazol-3-one.
$^1$H-NMR (DMSO-d6): δ 9.45 (bs, 2H), 8.00 (bs, 1H), 7.70 (m, 3H), 7.60 (s, 1H), 7.50 (m, 3H), 7.05 (d, 1H), 3.80 (s, 3H).

Example 21

4-[1-Aminomethylidene]-2-benzothiazol-2-yl-5-(3-bromothiophen-2-yl)-2,4-dihydropyrazol-3-one To a suspension of 628 mg NaH (15.70 mmol, 60% dispersion in mineral oil) in 25 ml of THF under a nitrogen atmosphere was slowly added diethyl carbonate (1.90 ml, 15.70 mmol) and 1-(3-bromo-thiophen-2-yl)-ethanone (1.61 g, 7.85 mmol). The reaction mixture was heated to 70° C. for 2 hours, cooled to room temperature poured into ice water followed by some AcOH and extracted with 2× EtOAc. The combined organic layers were washed with water 3×, washed with brine, dried over magnesium sulfate, evaporated and the residue was purified by column chromatography (silica, 25% EtOAc in PE (40/60) to give 1.54 g (5.84 mmol, 71%) of 3-(3-bromothiophen-2-yl)-3-oxo-propionic acid ethyl ester.

A solution of 918 mg (5.56 mmol) of benzothiazol-2-yl-hydrazine and 1.54 g (5.56 mmol) of 3-(3-bromothiophen-2-yl)-3-oxo-propionic acid ethyl ester in 25 ml of EtOH/AcOH (1:1) was refluxed overnight under a nitrogen atmosphere, cooled, the solids were filtered off, washed with EtOH and dried to give 711 mg (1.88 mmol, 34%) of 2-benzothiazol-2-yl-5-(3-bromothiophen-2-yl)-1,2-dihydropyrazol-3-one. $^1$H-NMR (DMSO-d6): δ 13.00 (bs, 1H), 8.10 (d, 1H), 7.90 (d, 1H), 7.70 (s, 1H), 7.50 (t, 1H), 7.40 (t, 1H), 7.20 (m, 1h), 6.30 (s, 1H).

To a solution of 700 mg (1.85 mmol) of 2-benzothiazol-2-yl-5-(3-bromothiophen-2-yl)-1,2-dihydropyrazol-3-one in 7 ml of THF was added N,N-dimethylformamide dimethylacetal (258 µl, 1.94 mmol). The reaction was stirred for 1 hour at room temperature under a nitrogen atmosphere after which the solids were filtered off, washed with diethyl ether and dried to give 550 mg (1.26 mmol, 69%) of 2-benzothiazol-2-yl-5-(3-bromothiophen-2-yl)-4-[1-dimethylaminomethylidene]-2,4-dihydropyrazol-3-one. $^1$H-NMR (DMSO-d6): δ 8.00 (d, 1H), 7.90 (d, 1H), 7.80 (d, 1H), 7.60 (s, 1H), 7.45 (t, 1H), 7.30 (m, 2H), 3.80 (s, 3H), 3.40 (s, 3H).

A suspension of 210 mg (0.485 mmol) of 2-benzothiazol-2-yl-5-(3-bromothiophen-2-yl)-4-[1-dimethylaminomethylidene]-2,4-dihydropyrazol-3-one in 5 ml 7N NH3 in MeOH was heated to 60° C. overnight. After cooling to room temperature, the solids were filtered, washed with a little EtOH and dried to give 198 mg (0.472 mmol, 97%) of 4-[1-aminomethylidene]-2-benzothiazol-2-yl-5-(3-bromothiophen-2-yl)-2,4-dihydropyrazol-3-one. $^1$H-NMR (DMSO-d6): δ 9.25 (bs, 2H), 8.05 (d, 1H), 7.85 (m, 3H), 7.45 (t, 1H), 7.30 (m, 2H).

Example 22

2-Benzothiazol-2-yl-4-[1-methylaminomethylidene]-5-thiophen-2-yl-2,4-dihydropyrazol-3-one To a suspension of 628 mg NaH (15.70 mmol, 60% dispersion in mineral oil) in 10 ml of THF under a nitrogen atmosphere was slowly added diethyl carbonate (1.90 ml, 15.70 mmol) and 2-acetylthiophene (1.00 g, 7.92 mmol). The reaction mixture was heated to 70° C. for 1 hour, cooled to room temperature poured into ice water, AcOH was added and the reaction mixture was with extracted twice with diethyl ether. The combined organic layers were washed with water, brine, dried over magnesium sulfate, evaporated and the residue was purified by column chromatography (silica, DCM) to give 1.27 g (6.41 mmol, 80%) of 3-oxo-3-thiophen-2-yl-propionic acid ethyl ester.

A solution of 1.06 g (6.41 mmol) of benzothiazol-2-yl-hydrazine and 1.27 g (6.41 mmol) of 3-oxo-3-thiophen-2-yl-propionic acid ethyl ester in 15 ml of EtOH was refluxed overnight under a nitrogen atmosphere, cooled, the solids were filtered off, washed with EtOH and dried to give 1.30 g (4.34 mmol, 68%) of 2-benzothiazol-2-yl-5-thiophen-2-yl-1,2-dihydropyrazol-3-one. $^1$H-NMR (DMSO-d6): δ 13.00 (bs, 1H), 8.05 (d, 1H), 7.90 (d, 1H), 7.70 (m, 2H), 7.50 (t, 1H), 7.40 (t, 1H), 7.20 (s, 1h), 6.00 (s, 1H).

To a solution of 137 mg (0.458 mmol) of 2-benzothiazol-2-yl-5-thiophen-2-yl-1,2-dihydropyrazol-3-one in 6 ml of THF was added N,N-dimethylformamide dimethylacetal (64 µl, 0.480 mmol). The reaction was stirred for 10 minutes at room temperature under a nitrogen atmosphere after which the solids were filtered off, washed with diethyl ether and dried to give 162 mg (0.458 mmol, 100%) of 2-benzothiazol-2-yl-4-[1-dimethylaminomethylidene]-5-thiophen-2-yl-2,4-dihydropyrazol-3-one. $^1$H-NMR (DMSO-d6): δ 8.00 (m, 2H), 7.85 (d, 1H), 7.75 (d, 1H), 7.55 (m, 1H), 7.45 (t, 1H), 7.30 (t, 1H), 7.20 (m, 1H), 3.80 (s, 3H), 3.45 (s, 3H).

A suspension of 162 mg (0.458 mmol) of 2-benzothiazol-2-yl-4-[1-dimethylaminomethylidene]-5-thiophen-2-yl-2,4-dihydropyrazol-3-one in 5 ml of 33% MeNH2 in EtOH was stirred at room temperature for 1.5 hours, the solids were filtered, washed with EtOH and dried to give 47 mg (0.138 mmol, 30%) of 2-benzothiazol-2-yl-4-[1-methylaminomethylidene]-5-thiophen-2-yl-2,4-dihydropyrazol-3-one.
¹H-NMR (DMSO-d6): δ 9.95 (bs, 1H), 8.20 (s, 1H), 8.00 (d, 1H), 7.85 (d, 1H), 7.75 (m, 2H), 7.45 (t, 1H), 7.35 (t, 1H), 7.20 (s, 1H), 3.30 (s, 3H).

Example 23

2-Benzothiazol-2-yl-5-methyl-4-[1-piperidin-1-ylmethylidene]-2,4-dihydropyrazol-3-one A solution of 2.00 g (12.10 mmol) of benzothiazol-2-ylhydrazine and 1.62 ml (12.71 mmol) of ethyl acetoacetate in 40 ml of acetic acid was refluxed under a nitrogen atmosphere for 2.5 hours and stirred at room temperature overnight. 50 ml of water was added and the precipitate was collected by filtration, washed with water and dried to give 2.68 g (11.59 mmol, 96%) of 2-benzothiazol-2-yl-5-methyl-1,2-dihydropyrazol-3-one. ¹H-NMR (DMSO-d6): δ 12.80 (bs, 1H), 8.00 (d, 1H), 7.80 (d, 1H), 7.50 (t, 1H), 7.35 (t, 1H), 5.25 (s, 1H), 2.20 (s, 3H).
To a suspension of 220 mg (0.951 mmol) of 2-benzothiazol-2-yl-5-methyl-1,2-dihydropyrazol-3-one in 20 ml toluene was added N,N-dimethylformamide dimethylacetal (135 µl, 1.00 mmol). The reaction was stirred for 4 hours at room temperature under a nitrogen atmosphere after which time the solvent was evaporated and the remaining solids were washed with diethyl ether and dried to give 180 mg (0.629 mmol, 66%) of 2-benzothiazol-2-yl-4-[1-dimethylaminomethylidene]-5-methyl-2,4-dihydropyrazol-3-one.
¹H-NMR (DMSO-d6): δ 7.95 (d, 1H), 7.75 (d, 1H), 7.65 (s, 1H), 7.40 (t, 1H), 7.25 (t, 1H), 3.75 (s, 3H), 3.40 (s, 3H), 2.20 (s, 3H).
To a suspension of 1.80 g (6.29 mmol) of 2-benzothiazol-2-yl-4-[1-dimethylaminomethylidene]-5-methyl-2,4-dihydropyrazol-3-one in a mixture of 15 ml of toluene and 10 ml of DMF was added 5 ml of a 4N NaOH solution. The reaction mixture was stirred under a nitrogen atmosphere at room temperature for 4 hours after which time the solids were filtered off and dried in vacuo to give 2-benzothiazol-2-yl-5-methyl-3-oxo-2,3-dihydro-1H-pyrazole-4-carbaldehyde (6.29 mmol; 100%). ¹H-NMR (DMSO-d6): δ 9.30 (s, 1H), 8.45 (s, 1H), 7.90 (d, 1H), 7.70 (d, 1H), 7.40 (t, 1H), 7.20 (t, 1H), 2.20 (2, 3H).
A mixture of 160 mg (0.617 mmol) of 2-benzothiazol-2-yl-5-methyl-3-oxo-2,3-dihydro-1H-pyrazole-4-carbaldehyde, piperidine (720 µl, 7.35 mmol) and 2 drops of concentrated HCl was refluxed overnight under a nitrogen atmosphere, cooled, evaporated to dryness and the residue purified by column chromatography (silica, 4% methanol in dichloromethane) to give 100 mg (0.306 mmol, 50%) of 2-benzothiazol-2-yl-5-methyl-4-[1-piperidin-1-yl-methylidene]-2,4-dihydropyrazol-3-one. ¹H-NMR (DMSO-d6): δ 7.95 (d, 1H), 7.75 (d, 1H), 7.65 (s, 1H), 7.40 (t, 1H), 7.25 (t, 1H), 4.50 (bs, 2H), 3.75 (bs, 2H), 2.00 (s, 3H), 1.70 (bs, 4H), 1.65 (bs, 2H).

Example 24

Biological Methods

The PC-3 prostate cancer cell line (ATCC# CRL-1435) was maintained in RPMI-1640 medium (Invitrogen, 31870), supplemented with 10% Fetal Bovine Serum (Sigma, F7524), L-Glutamine (Invitrogen 25030-024). Cells were split once a week at a 1:10 ratio.

Example 25

Cell Invasion Assay

For cell invasion assays, PC3 cells were incubated in the presence of a compound according to the invention (10 uM) for 4 days, prior to the invasion assay. Forty thousand cells were seeded into BD Biocoat Matrigel Invasion chambers (8 micron; BD 354480) in serum-free medium. The invasion chamber was placed in a 24-well containing medium with 10% fetal calf serum as chemo-attractant. As a control, the same amount of cells was seeded in 24-well culture plates. After 48 hours incubation, cells in the invasion chamber were removed by aspiration and cleaning the inner compartment with a cotton swab. The invasion chamber was then put into CellTiter-GLO (CTG, Promega-G7571) cell viability reagent, incubated for 15 minutes, and then analyzed on a Victor3 luminometer. Cell invasion was calculated as the CTG activity on the lower part of the membrane divided by the CTG activity of the cells grown in a 24 well plate. Inhibition of cell invasion by a specific compound was estimated by comparing the amount of cell invasion of compound-treated cells versus DMSO treated cells.

The invention claimed is:
1. A method for the treatment of carcinoma, the method comprising:
administering to a subject suffering from carcinoma a compound having the structure according to formula III:

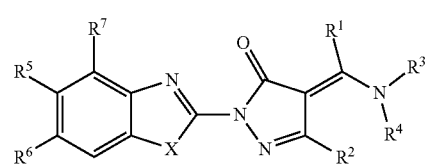

formula III wherein:
X is NH or S;
$R^1$ is H or (1C-4C)alkyl;
$R^2$ is (1C-4C)alkyl, phenyl, or a monocyclic aromatic ring having one or more N—, O— or S— atoms in the ring, wherein the (1C-4C)alkyl, phenyl, or monocyclic aromatic ring is unsubstituted or substituted;
$R^3$ and $R^4$ are each independently H, (1C-6C)alkyl, (2C-6C) alkenyl, (2C-6C)alkynyl, cyano, a monocyclic aromatic ring having one or more N—, O— or S— atoms in the ring, a monocyclic non-aromatic ring having one or more N—, O— or S— atoms in the ring, wherein each is unsubsituted or substituted;
or $R^3$ and $R^4$ form together a pyrrolyl, imidazolyl, pyrazolyl, pyrrolidinyl, pyrrolinylimidazolidinyl, imidazolinyl, piperidyl, or piperazinylmorpholinyl, wherein each is unsubstituted or substituted;
or wherein $R^3$ and $R^4$ each independently represent hydrogen, methyl, ethyl or propyl or a group selected from list of structures consisting of:

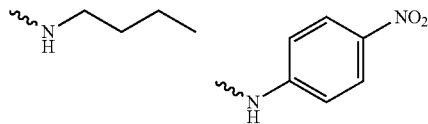

-continued

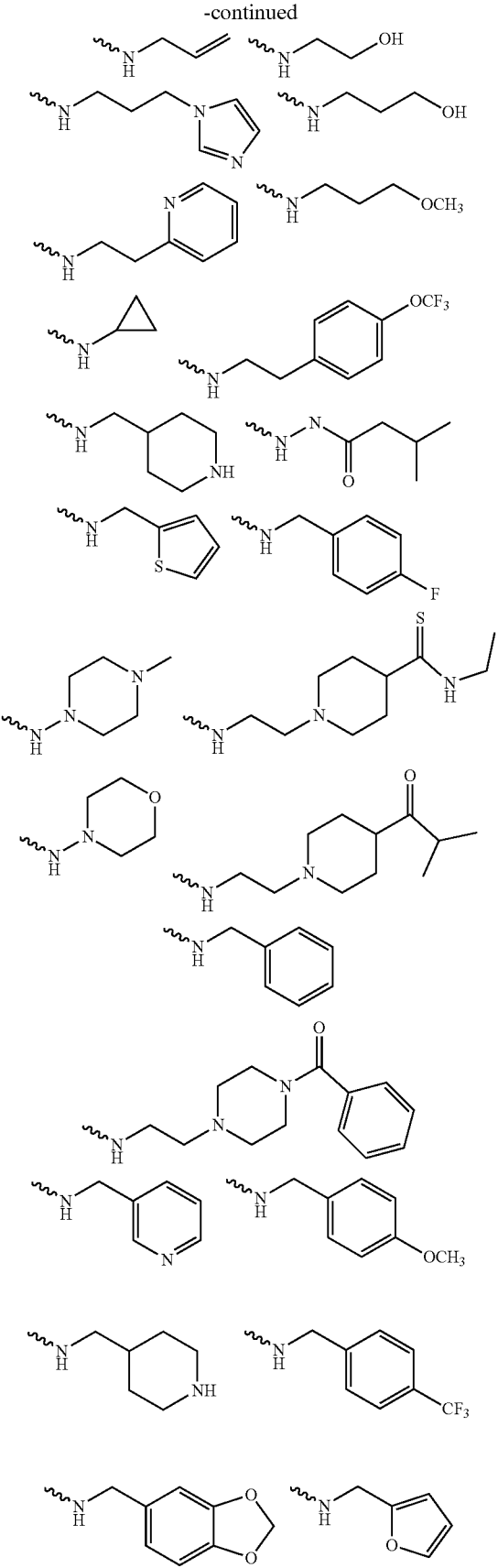

or R³ and R⁴ form together a substituted ring as represented in the following structures:

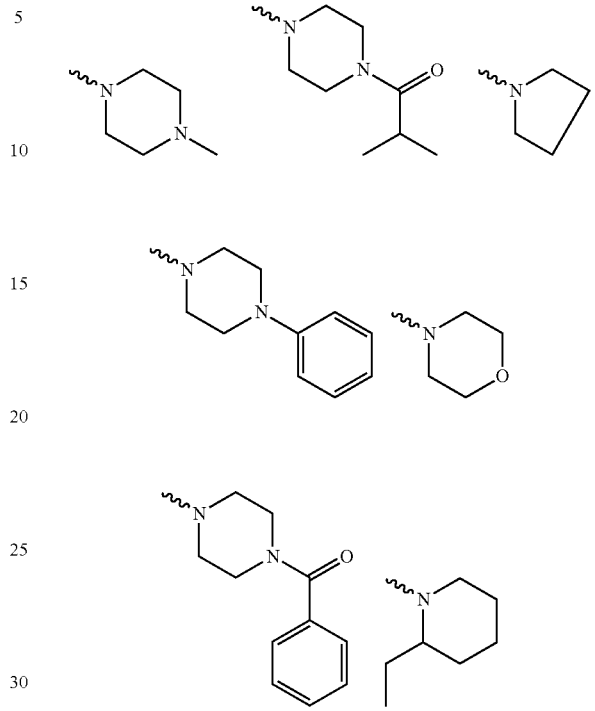

$R^5$ is H, Cl, F, Br, Me, $NO_2$, t-butyl, $OCF_3$, $OCH_3$, or $CF_3$;
$R^6$ is H, (1C-4C)alkyl, (1C-4C)alkyloxy, halo(1C-4C)alkyl, halo(1C-4C)alkyloxy, nitro or halogen;
$R^7$ is H, F, Cl, Br, Me, $NO_2$, t-butyl, $OCF_3$, $OCH_3$, or $CF_3$;
or a pharmaceutically acceptable addition salt thereof.

2. The method according to claim 1, wherein:
$R^5$ and $R^6$ are hydrogen;
$R^7$ is H.

3. The method according to claim 1, wherein X is S.

4. The method according to claim 1, wherein $R^1$ is H or (1C-4C)alkyl and $R^2$ is (1C-4C)alkyl or phenyl.

5. The method according to claim 1, wherein $R^3$ is hydrogen.

6. The method according to claim 1, wherein $R^3$ and $R^4$ represent both methyl or $R^3$ is hydrogen.

7. The method according to claim 1, wherein the compound according to formula III is a compound having a structure according to formula II:

formula II

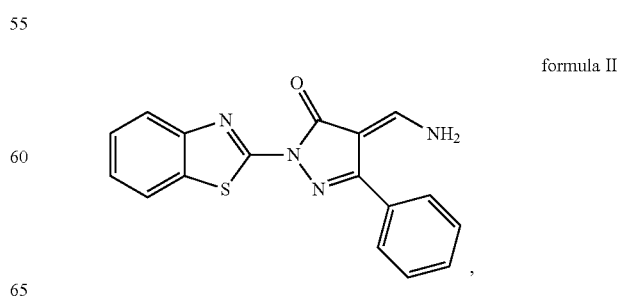

or a pharmaceutically acceptable addition salt thereof.

8. A method for the treatment of carcinoma, the method comprising:
administering to a subject suffering from carcinoma a compound having the structure according to formula I:

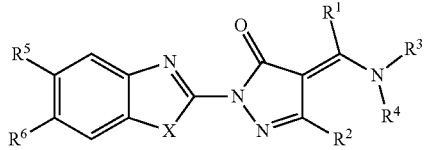

Formula I wherein:
X is NH or S;
$R^1$ is H or (1C-4C)alkyl;
$R^2$ is —Z or —Y—Z, wherein Y is —CH$_2$— or —CH$_2$—CH$_2$—, and Z is thien-2-yl, N—methylpyrol-3-yl, benzo[b]thien-2-yl, 2-naphthalenyl, phenyl, or a monocyclic aromatic ring having one or more N—, O— or S— atoms in the ring, and wherein Z is unsubstituted or substituted;
$R^3$ and $R^4$ are each independently H, (1 C-6C)alkyl, (2C-6C) alkenyl, (2C-6C)alkynyl, cyano, (3C-6C)cycloalkyl, a monocyclic aromatic ring having one or more N—, O— or S— atoms in the ring, a monocyclic non-aromatic ring having one or more N—, O— or S— atoms in the ring, wherein each is unsubsituted or substituted;
or $R^3$ and $R^4$ form together a pyrrolyl, imidazolyl, pyrazolyl, pyrrolidinyl, pyrrolinylimidazolidinyl, imidazolinyl, piperidyl, piperazinylmorpholinyl, wherein each is unsubstituted or substituted;
$R^5$ is H or CF$_3$;
$R^6$ is H, (1C-4C)alkyl, (1C-4C)alkyloxy, halo(1C-4C)alkyl, halo(1C-4C)alkyloxy, nitro or halogen;
or a pharmaceutically acceptable addition salt thereof.

9. The method according to claim 1, wherein the compound according to formula III is a compound according to formula I:

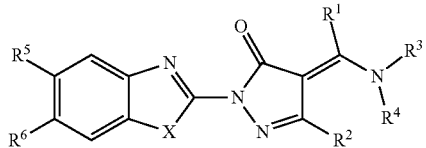

Formula I wherein:
$R^2$ is a substituted or unsubstituted monocyclic aromatic ring having one or more N—, O— or S— atoms in the ring;
$R^5$ is H or CF$_3$;
or a pharmaceutically acceptable addition salt thereof.

10. The method according to claim 8, wherein:
X is S;
$R^1$ is H;
$R^2$ is Z and Z is substituted or unsubstituted phenyl;
or Z is substituted or unsubstituted thien-2-yl;
or Z is N-methylpyrol-3-yl or benzo[b]thien-2-yl or 2-naphthalenyl;
$R^3$,$R^4$ are H,H or H,CH$_3$ or CH$_3$,CH$_3$;

$R^5$ is H;
$R^6$ is H, halogen or methoxy;
or a pharmaceutically acceptable addition salt thereof.

11. The method according to claim 8, wherein $R^6$ is methoxy.

12. A method for the treatment of carcinoma, the method comprising:
administering to a subject suffering from carcinoma a compound having the structure according to formula III:

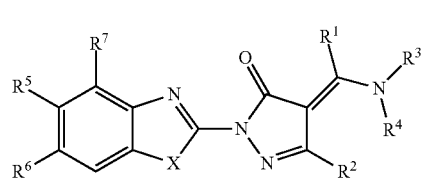

formula III wherein:
X is S;
$R^1$ is H, or CH$_3$;
$R^2$ is CF$_3$, CH$_3$, phenylethyl,

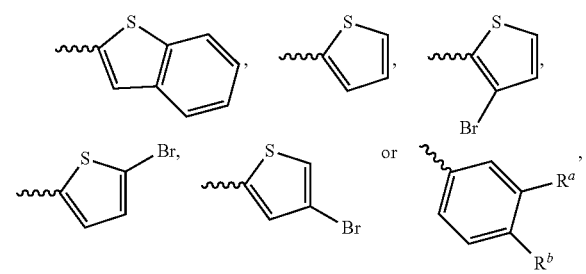

wherein $R^a$ is H, F, Cl, Br, I, NO$_2$, methyl, ethyl, isopropyl, t-butyl, methoxy or CF$_3$ and $R^b$ is H, Cl or CH$_3$;
$R^3$, $R^4$ is H, H or H, CH$_3$, or CH$_3$, CH$_3$ or one of $R^3$ or $R^4$ is —CN or p-methoxyphenylmethyl or $R^3$ and $R^4$ together represent a ring

on the nitrogen of Formula III to represent a piperidyl or $R^3$ and $R^4$ together represent a ring

on the nitrogen of Formula III to pyrrolidinyl, or $R^3$ is methyl and $R^4$ is dichlorbenzyl

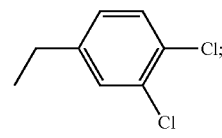

$R^5$ is H, Cl, F, Br, Me, NO$_2$, t-butyl, OCF$_3$, OCH$_3$, or CF$_3$,
$R^6$ is H, F, Cl, Br, NO$_2$, CH$_3$, t-butyl, OCH$_3$, OCF$_3$, or CF$_3$;
R7 is H, F, Cl, Br, Me, NO2, t-butyl, OCF3, OCH3, or CF3,
or a pharmaceutically acceptable addition salt thereof.

13. The method according to claim 12, wherein:
$R^2$ is CF$_3$, CH$_3$, phenylethyl,

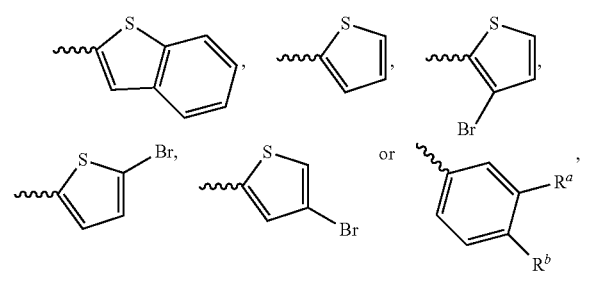

wherein $R^a$ is H, F, Cl, Br, I, NO$_2$, methyl, ethyl, isopropyl, t-butyl, methoxy or CF$_3$ and $R^b$ is H, Cl or CH$_3$;
$R^3$, $R^4$ is H, H or H, CH$_3$, or CH$_3$, CH$_3$ or one of $R^3$ or $R^4$ is —CN or p-methoxyphenylmethyl or $R^3$ and $R^4$ together represent a ring

on the nitrogen of Formula III to represent a piperidyl or $R^3$ and $R^4$ together represent a ring

on the nitrogen of Formula III to pyrrolidinyl, or $R^3$ is methyl and $R^4$ is dichlorbenzyl

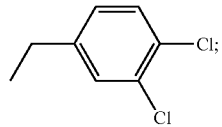

$R^5$ is H, or Cl;
$R^6$ is H, F, Cl, NO$_2$, CH$_3$, t-butyl, OCH$_3$ or OCF$_3$;
$R^7$ is H, or Cl;
or a pharmaceutically acceptable addition salt thereof.

14. The method according to claim 12, wherein:
$R^1$ is H;
$R^2$ is CF$_3$, CH$_3$, phenylethyl,

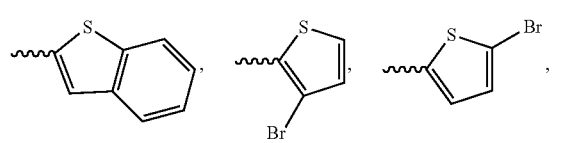

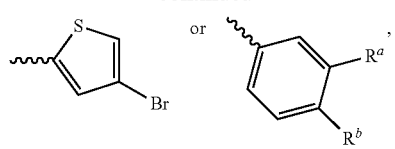

wherein $R^a$ is H, F, Cl, Br, I, NO$_2$, methyl, ethyl, isopropyl, t-butyl, methoxy or CF$_3$ and $R^b$ is H, Cl or CH$_3$;
$R^3$, $R^4$ is H, H or H, CH$_3$, or together represent a ring

on the nitrogen of Formula III to represent piperidyl, or $R^3$ is methyl and $R^4$ is dichlorbenzyl

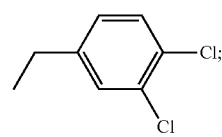

$R^5$ is H;
$R^6$ is H, Cl, NO$_2$, CH$_3$, OCH$_3$, OCF$_3$;
$R^7$ is H.

15. The method according to claim 12, wherein:
$R^1$ H;
$R^2$ is CF$_3$, CH$_3$,

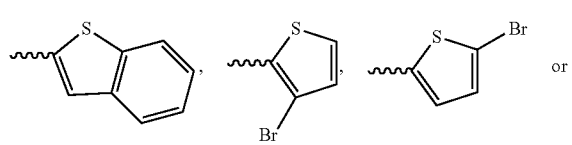

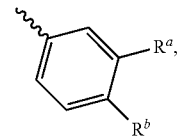

wherein $R^a$ is H, F, Cl, Br, I, methyl, ethyl, isopropyl, t-butyl or CF$_3$ and $R^b$ is H, Cl or CH$_3$;
$R^3$, $R^4$ is H, H or H, CH$_3$, or together represent a ring

on the nitrogen of Formula III to represent piperidyl, or R³ is methyl and R⁴ is dichlorbenzyl

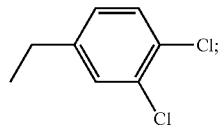

R⁵ is H;
R⁶ is H, Cl, NO₂, CH₃, OCH₃, OCF₃;
R⁷ is H;
or a pharmaceutically acceptable addition salt thereof.

16. The method according to claim 1, wherein the carcinoma is selected from the group consisting of gastric cancer, bladder cancer, esophageal cancer, breast cancer, prostate cancer and pancreas cancer.

17. The method according to claim 16 wherein the carcinoma is prostate cancer.

18. The method according to claim 1, wherein the treatment results in delaying, preventing, treating or reversing metastasis.

19. The method according to claim 1, wherein the alkyl, phenyl or aromatic ring of R² is substituted with one or more groups selected from the group consisting of (1C-4C)alkyl, (1C-4C)alkyloxy, halo(1C-4C)alkyl, halo(1C-4C)alkyloxy, phenyloxy, phenylthio, halogen, and nitro.

20. The method according to claim 1, wherein R³ is a (1C-6C)alkyl, (2C-6C) alkenyl, (2C-6C)alkynyl, cyano, (3C-6C)cycloalkyl, phenyl, a monocyclic aromatic ring having one or more N—, O— or S— atoms in the ring, a monocyclic non-aromatic ring having one or more N—, O— or S— atoms in the ring and wherein R³ is substituted with a hydroxyl, (1C-4C)alkoxy, phenyl, cycloalkyl, piperidyl, piperazinyl, furyl, thienyl, pirazinyl, pyrrolyl, 2H-pyrrolyl, pyrazolyl, isoxazolyl, isothiazolyl, pyrrolidonyl, pyrrolinyl, imidazolinyl, imidazolyl, or monocyclic aromatic ring having one or more N—, O— or S— atoms in the ring, wherein each substitution is unsubstituted or further substituted.

21. The method according to claim 20, wherein the substitution hydroxyl, (1C-4C)alkoxy, phenyl, cycloalkyl, piperidyl, piperazinyl, furyl, thienyl, pirazinyl, pyrrolyl, 2H-pyrrolyl, pyrazolyl, isoxazolyl, isothiazolyl, pyrrolidonyl, pyrrolinyl, imidazolinyl, imidazolyl, or monocyclic aromatic ring having one or more N—, O— or S— atoms in the ring is further substituted with (1C-4C)alkyl, (1C-4C)alkyloxy, halo(1C-4C)alkyl, halo(1C-4C)alkyloxy, halogen, nitro or (1C-2C)dioxol forming a ring.

22. The method according to claim 1, wherein R⁴ is a (1C-6C)alkyl, (2C-6C) alkenyl, (2C-6C)alkynyl, cyano, (3C-6C)cycloalkyl, phenyl, a monocyclic aromatic ring having one or more N—, O— or S— atoms in the ring, a monocyclic non-aromatic ring having one or more N—, O— or S— atoms in the ring and wherein R⁴ is substituted with a hydroxyl, (1C-4C)alkoxy, phenyl, cycloalkyl, piperidyl, piperazinyl, furyl, thienyl, pirazinyl, pyrrolyl, 2H-pyrrolyl, pyrazolyl, isoxazolyl, isothiazolyl, pyrrolidonyl, pyrrolinyl, imidazolinyl, imidazolyl, or monocyclic aromatic ring having one or more N—, O— or S— atoms in the ring, wherein each substitution is unsubstituted or further substituted.

23. The method according to claim 22, wherein the substitution hydroxyl, (1C-4C)alkoxy, phenyl, cycloalkyl, piperidyl, piperazinyl, furyl, thienyl, pirazinyl, pyrrolyl, 2H-pyrrolyl, pyrazolyl, isoxazolyl, isothiazolyl, pyrrolidonyl, pyrrolinyl, imidazolinyl, imidazolyl, or monocyclic aromatic ring having one or more N—, O— or S— atoms in the ring is further substituted with (1C-4C)alkyl, (1C-4C)alkyloxy, halo(1C-4C)alkyl, halo(1C-4C)alkyloxy, halogen, nitro or (1C-2C)dioxol forming a ring.

24. The method according to claim 1, wherein R³ and R⁴ form together a pyrrolyl, imidazolyl, pyrazolyl, pyrrolidinyl, pyrrolinylimidazolidinyl, imidazolinyl, piperidyl, or piperazinylmorpholinyl, wherein each of the foregoing is substituted with (1C-6C)alkyl, phenyl(1C-4C)alkyl, or phenylketo (1C-4C)alkyl.

25. The method according to claim 2, wherein alkyl, phenyl or aromatic ring of R² is substituted with one or more groups selected from the group consisting of a (1C-4C)alkyl and a halogen.

26. The method according to claim 8, wherein Z is phenyl or a monocyclic aromatic ring having one or more N—, O— or S— atoms in the ring, and wherein Z is substituted with one or more groups selected from the group consisting of (1 C-4C)alkyl, (1 C-4C)alkyloxy, halo(1C-4C)alkyl, halo(1C-4C)alkyloxy, phenyloxy, phenylthio, halogen, or nitro from (1C-4C)alkyl, (1C-4C)alkyloxy, halo(1C-4C)alkyl, halo (1C-4C)alkyloxy, phenyloxy, phenylthio, halogen, and nitro.

27. The method according to claim 8, wherein Z is thien-2-yl substituted at position 3, 4 or 5 with a halogen.

28. The method according to claim 8, wherein R³ is (1C-6C)alkyl, (2C-6C) alkenyl, (2C-6C)alkynyl, cyano, (3C-6C)cycloalkyl, a monocyclic aromatic ring having one or more N—, O— or S— atoms in the ring, a monocyclic non-aromatic ring having one or more N—, O— or S— atoms in the ring and wherein R³ is substituted with a hydroxyl, (1C-4C)alkoxy, cycloalkyl, piperidyl, piperazinyl, furyl, thienyl, pirazinyl, pyrrolyl, 2H-pyrrolyl, pyrazolyl, isoxazolyl, isothiazolyl, pyrrolidonyl, pyrrolinyl, imidazolinyl, imidazolyl, or a monocyclic aromatic ring having one or more N—, O— or S— atoms in the ring, wherein each substitution is unsubstituted or further substituted.

29. The method according to claim 28, wherein the substitution hydroxyl, (1C-4C)alkoxy, cycloalkyl, piperidyl, piperazinyl, furyl, thienyl, pirazinyl, pyrrolyl, 2H-pyrrolyl, pyrazolyl, isoxazolyl, isothiazolyl, pyrrolidonyl, pyrrolinyl, imidazolinyl, imidazolyl, or a monocyclic aromatic ring having one or more N—, O— or S— atoms in the ring is further substituted with (1C-4C)alkyl, (1C-4C)alkyloxy, halo(1C-4C)alkyl, halo(1C-4C)alkyloxy, halogen, nitro or (1C-2C)dioxol forming a ring.

30. The method according to claim 8, wherein R⁴ is (1C-6C)alkyl, (2C-6C) alkenyl, (2C-6C)alkynyl, cyano, (3C-6C)cycloalkyl, a monocyclic aromatic ring having one or more N—, O— or S— atoms in the ring, a monocyclic non-aromatic ring having one or more N—, O— or S— atoms in the ring and wherein R⁴ is substituted with a hydroxyl, (1C-4C)alkoxy, cycloalkyl, piperidyl, piperazinyl, furyl, thienyl, pirazinyl, pyrrolyl, 2H-pyrrolyl, pyrazolyl, isoxazolyl, isothiazolyl, pyrrolidonyl, pyrrolinyl, imidazolinyl, imidazolyl, or a monocyclic aromatic ring having one or more N—, O— or S— atoms in the ring, wherein each substitution is unsubstituted or further substituted.

31. The method according to claim 30, wherein the substitution hydroxyl, (1C-4C)alkoxy, cycloalkyl, piperidyl, piperazinyl, furyl, thienyl, pirazinyl, pyrrolyl, 2H-pyrrolyl, pyrazolyl, isoxazolyl, isothiazolyl, pyrrolidonyl, pyrrolinyl, imidazolinyl, imidazolyl, a monocyclic aromatic ring having one or more N—, O— or S— atoms in the ring is further substituted with (1 C-4C)alkyl, (1 C-4C)alkyloxy, halo(1C-4C)alkyl, halo(1C-4C)alkyloxy, halogen, nitro or (1C-2C) dioxol forming a ring.

32. The method according to claim 8, wherein R³ and R⁴ form together a pyrrolyl, imidazolyl, pyrazolyl, pyrrolidinyl, pyrrolinylimidazolidinyl, imidazolinyl, piperidyl, or piperazinylmorpholinyl, wherein each of the foregoing is substituted with (1C-6C)alkyl, phenyl(1C-4C)alkyl, or phenylketo (1C-4C)alkyl.

33. The method according to claim 9, wherein the aromatic ring of R² is substituted with one or more groups selected from the group consisting of (1 C-4C)alkyl, (1C-4C)alkyloxy, halo(1C-4C)alkyl, halo(1C-4C)alkyloxy, phenyloxy, phenylthio, halogen, and nitro.

34. The method according to claim 9, wherein R³ is a (1C-6C)alkyl, (2C-6C) alkenyl, (2C-6C)alkynyl, cyano, (3C-6C)cycloalkyl, a monocyclic non-aromatic ring having one or more N—, O— or S— atoms in the ring and wherein R³ is substituted with a hydroxyl, (1C-4C)alkoxy, cycloalkyl, piperidyl, piperazinyl, furyl, thienyl, pyrrolyl, 2H-pyrrolyl, pyrazolyl, isoxazolyl, isothiazolyl, pyrrolidonyl, pyrrolinyl, imidazolinyl, or imidazolyl, wherein each substitution is unsubstituted or further substituted.

35. The method according to claim 34, wherein the substitution hydroxyl, (1C-4C)alkoxy, cycloalkyl, piperidyl, piperazinyl, furyl, thienyl, pyrrolyl, 2H-pyrrolyl, pyrazolyl, isoxazolyl, isothiazolyl, pyrrolidonyl, pyrrolinyl, imidazolinyl, imidazolyl is further substituted with (1C-4C)alkyl, (1C-4C)alkyloxy, halo(1C-4C)alkyl, halo(1C-4C)alkyloxy, halogen, nitro or (1C-2C)dioxol forming a ring.

36. The method according to claim 9, wherein R⁴ is a (1C-6C)alkyl, (2C-6C) alkenyl, (2C-6C)alkynyl, cyano, (3C-6C)cycloalkyl, a monocyclic non-aromatic ring having one or more N—, O— or S— atoms in the ring and wherein R⁴ is substituted with a hydroxyl, (1C-4C)alkoxy, cycloalkyl, piperidyl, piperazinyl, furyl, thienyl, pyrrolyl, 2H-pyrrolyl, pyrazolyl, isoxazolyl, isothiazolyl, pyrrolidonyl, pyrrolinyl, imidazolinyl, or imidazolyl wherein each substitution is unsubstituted or further substituted.

37. The method according to claim 36, wherein the substitution hydroxyl, (1C-4C)alkoxy, cycloalkyl, piperidyl, piperazinyl, furyl, thienyl, pyrrolyl, 2H-pyrrolyl, pyrazolyl, isoxazolyl, isothiazolyl, pyrrolidonyl, pyrrolinyl, imidazolinyl, imidazolyl is further substituted with (1C-4C)alkyl, (1C-4C)alkyloxy, halo(1C-4C)alkyl, halo(1C-4C)alkyloxy, halogen, nitro or (1C-2C)dioxol forming a ring.

38. The method according to claim 9, wherein R³ and R⁴ form together a pyrrolyl, imidazolyl, pyrazolyl, pyrrolidinyl, pyrrolinylimidazolidinyl, imidazolinyl, piperidyl, piperazinylmorpholinyl, wherein each of the foregoing is substituted with (1C-6C)alkyl, phenyl(1C-4C)alkyl, or phenylketo(1C-4C)alkyl.

39. The method according to claim 10, wherein Z is phenyl and is substituted at meta or para position, or at both positions, with one or two substituents selected from the group consisting of —NO₂, halogen, CF₃, (1C-4C)alkyl and methoxy.

40. The method according to claim 10, wherein Z is thien-2-yl, and is substituted at least one of positions 3, 4 and 5 with halogen.

41. A method for treating a subject having a carcinoma, the method comprising:
administering to the subject a compound having the structure according to formula IV:

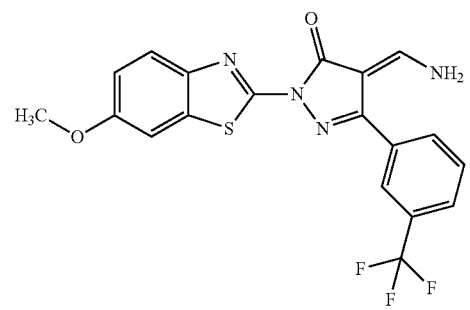

Formula IV or a pharmaceutically acceptable addition salt thereof.

42. A method for treating a subject having a carcinoma, the method comprising:
administering to the subject a compound having the structure according to formula V:

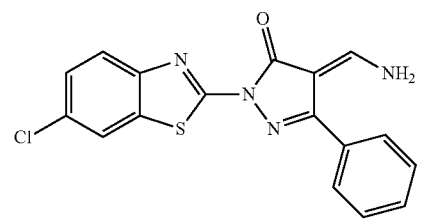

Formula V or a pharmaceutically acceptable addition salt thereof.

* * * * *

UNITED STATES PATENT AND TRADEMARK OFFICE
CERTIFICATE OF CORRECTION

PATENT NO.         : 9,453,012 B2                                             Page 1 of 1
APPLICATION NO.    : 14/383083
DATED              : September 27, 2016
INVENTOR(S)        : Onno Van Hooij et al.

It is certified that error appears in the above-identified patent and that said Letters Patent is hereby corrected as shown below:

In the Claims

| | |
|---|---|
| Claim 8, Column 47, Line 24, | change "(1 C-6C)alkyl," to --(1C-6C)alkyl,-- |
| Claim 14, Column 50, Lines 11, 12, | change "and $R^{ID}$ is H, Cl or $CH_3$;" to --and $R^b$ is H, Cl or $CH_3$;-- |
| Claim 26, Column 52, Line 20, | change "(1 C-4C)alkyloxy," to --(1C-4C)alkyloxy,-- |
| Claim 30, Column 52, Line 48, | change "(2C-6C) alkenyl," to --(2C-6C)alkenyl,-- |
| Claim 31, Column 52, Line 65, | change "(1 C-4C)alkyl, (1 C-4C)alkyloxy," to --(1C-4C)alkyl, (1C-4C)alkyloxy,-- |
| Claim 33, Column 53, Line 9, | change "(1 C-4C)alkyl," to --(1C-4C)alkyl,-- |

Signed and Sealed this
Seventh Day of March, 2017

Michelle K. Lee
*Director of the United States Patent and Trademark Office*